(12) United States Patent
Armstrong et al.

(10) Patent No.: US 8,501,217 B2
(45) Date of Patent: Aug. 6, 2013

(54) IMPLANTABLE GRAFT TO CLOSE A FISTULA

(75) Inventors: David N. Armstrong, Atlanta, GA (US); Brain L. Bates, Bloomington, IN (US); Mark W. Bleyer, West Lafayette, IN (US); F. Joseph Obermiller, West Lafayette, IN (US); Umesh H. Patel, West Lafayette, IN (US)

(73) Assignees: Cook Medical Technologies LLC, Bloomington, IN (US); Cook Biotech Incorporated, West Lafayette, IN (US)

( * ) Notice: Subject to any disclaimer, the term of this patent is extended or adjusted under 35 U.S.C. 154(b) by 22 days.

(21) Appl. No.: 13/018,582

(22) Filed: Feb. 1, 2011

(65) Prior Publication Data

US 2011/0125289 A1     May 26, 2011

Related U.S. Application Data

(63) Continuation of application No. 11/472,642, filed on Jun. 21, 2006, now Pat. No. 7,897,167.

(60) Provisional application No. 60/692,694, filed on Jun. 21, 2005.

(51) Int. Cl.
    *A61F 2/02*          (2006.01)
(52) U.S. Cl.
    USPC ........................................ 424/426
(58) Field of Classification Search
    None
    See application file for complete search history.

(56) References Cited

U.S. PATENT DOCUMENTS

| | | | |
|---|---|---|---|
| 2,127,903 | A | 8/1938 | Bowen |
| 3,996,921 | A | 12/1976 | Neuwirth |
| 4,511,653 | A | 4/1985 | Play |
| 4,902,508 | A | 2/1990 | Badylak et al. |
| 4,956,178 | A | 9/1990 | Badylak et al. |

(Continued)

FOREIGN PATENT DOCUMENTS

| | | |
|---|---|---|
| EP | 0894 474 A1 | 2/1999 |
| RU | 2180529 | 8/1999 |

(Continued)

OTHER PUBLICATIONS

David J. Schultz et al., "Procine Small Intestine Submucosa as a Treatment for Enterocutaneous Fistulas", J Am. Coll. Surg. pp. 541-543 (2002).

(Continued)

*Primary Examiner* — Allison Ford
(74) *Attorney, Agent, or Firm* — Brinks Hofer Gilson & Lione

(57) ABSTRACT

An implantable graft, which may be inserted into a fistula tract to occlude the primary opening of the fistula, is provided. To prevent unintentional displacement of the graft or extrusion of the graft from the fistula of a patient, the graft may be provided with a cap that extends laterally from at least one end of the body of the graft, where the cap may be integral with the body of the graft, attachable to at least one end of the body of the graft, and/or moveable along the body of the graft. The graft may also have a tail that extends from one end of the body of the graft to assist in placement of the graft in a fistula tract. The graft may be an integral unit made of a single material, such as a heterograft material, or may include distinct components made of the same or different materials. Methods for closing a fistula tract are also provided.

19 Claims, 9 Drawing Sheets

U.S. PATENT DOCUMENTS

| | | | |
|---|---|---|---|
| 5,192,301 A | 3/1993 | Kamiya | |
| 5,275,826 A | 1/1994 | Badylak et al. | |
| 5,281,422 A | 1/1994 | Badylak et al. | |
| 5,330,503 A | 7/1994 | Yoon | |
| 5,345,948 A | 9/1994 | O'Donnell, Jr. | |
| 5,374,261 A | 12/1994 | Yoon | |
| RE34,866 E | 2/1995 | Kensey et al. | |
| 5,514,158 A | 5/1996 | Kanesaka | |
| 5,516,533 A | 5/1996 | Badylak et al. | |
| 5,522,840 A | 6/1996 | Krajicek | |
| 5,554,389 A | 9/1996 | Badylak | |
| 5,584,827 A | 12/1996 | Korteweg et al. | |
| 5,620,461 A | 4/1997 | Muijs Van De Moer | |
| 5,628,762 A | 5/1997 | Al-Tameem | |
| 5,643,305 A | 7/1997 | Al-Tameem | |
| 5,733,337 A | 3/1998 | Carr, Jr. et al. | |
| 5,752,974 A | 5/1998 | Rhee et al. | |
| 5,755,791 A | 5/1998 | Whitson et al. | |
| 5,846,183 A | 12/1998 | Chilcoat | |
| 5,860,978 A | 1/1999 | McDevitt et al. | |
| 5,947,994 A | 9/1999 | Louw et al. | |
| 5,955,110 A | 9/1999 | Patel et al. | |
| 5,993,844 A | 11/1999 | Abraham et al. | |
| 5,997,575 A | 12/1999 | Whitson et al. | |
| 6,090,996 A | 7/2000 | Li | |
| 6,099,567 A | 8/2000 | Badylak et al. | |
| 6,149,581 A | 11/2000 | Klingenstein | |
| 6,270,515 B1 | 8/2001 | Linden | |
| 6,296,632 B1 | 10/2001 | Luscher et al. | |
| 6,315,787 B1 | 11/2001 | Tsugita et al. | |
| 6,331,319 B1 | 12/2001 | Badylak et al. | |
| 6,475,232 B1 | 11/2002 | Babbs et al. | |
| 6,602,931 B2 | 8/2003 | Chen et al. | |
| 6,638,312 B2 | 10/2003 | Plouhar et al. | |
| 6,666,892 B2 | 12/2003 | Hiles | |
| 6,800,056 B2 | 10/2004 | Tartaglia et al. | |
| 2001/0027347 A1 | 10/2001 | Rousseau | |
| 2003/0013989 A1 | 1/2003 | Obermiller et al. | |
| 2003/0051735 A1 | 3/2003 | Pavcnik et al. | |
| 2004/0064017 A1 | 4/2004 | Cappiello et al. | |
| 2005/0013844 A1 | 1/2005 | Hadlock et al. | |
| 2005/0049626 A1 | 3/2005 | Burgard | |
| 2005/0070759 A1 | 3/2005 | Armstrong | |
| 2005/0113937 A1 | 5/2005 | Binette et al. | |
| 2005/0155608 A1 | 7/2005 | Pavcnik et al. | |
| 2005/0159776 A1 | 7/2005 | Armstrong | |
| 2005/0182495 A1 | 8/2005 | Perrone | |
| 2005/0288787 A1 | 12/2005 | Crawley | |
| 2006/0015142 A1 | 1/2006 | Malazgirt | |
| 2006/0074447 A2 | 4/2006 | Armstrong | |
| 2007/0088445 A1 | 4/2007 | Patel et al. | |
| 2008/0004657 A1 | 1/2008 | Obermiller et al. | |

FOREIGN PATENT DOCUMENTS

| | | |
|---|---|---|
| SU | 1718837 | 3/1992 |
| WO | WO 90/14796 | 12/1990 |
| WO | WO 93/16658 | 9/1993 |
| WO | WO 97/41778 | 11/1997 |
| WO | WO 98/01088 | 1/1998 |
| WO | WO 98/22158 | 5/1998 |
| WO | WO 98/25637 | 6/1998 |
| WO | WO 99/32049 | 7/1999 |
| WO | WO 00/74576 | 12/2000 |
| WO | WO 01/56475 A1 | 2/2001 |
| WO | WO 02/74192 A2 | 2/2002 |
| WO | WO 02/062234 A2 | 8/2002 |
| WO | WO 03/002165 | 1/2003 |
| WO | WO 2004/012627 A1 | 2/2004 |
| WO | WO 2004/112644 A2 | 6/2004 |
| WO | WO 2004/103187 | 12/2004 |
| WO | WO 2004/112644 A2 | 12/2004 |
| WO | WO 2005/020823 | 3/2005 |
| WO | WO 2005/020847 | 3/2005 |
| WO | WO 2005/030035 | 4/2005 |
| WO | WO 2005/053617 A2 | 6/2005 |
| WO | WO 2005/070489 | 8/2005 |
| WO | WO 2006/119256 A | 11/2006 |

OTHER PUBLICATIONS

J. R. Miklos et al., "Rectovaginal Fistula Repair Utilizing a Cadaveric Dermal Allograft" Int. Urogynecol. J. 10: pp. 405-406 (1999).

Search Report for PCT/US2006/045890, May 23, 2007.

Sentovic Stephen M. "Fibrin glue for anal fistulas." Dis Colon Rectum 2003; 46;498-502.

Lindsay I, Smilgin-Humphreys MM, Cunningham C, Morensen NJM, George B. "A randomized, controlled trial of fibrin glue vs conventional treatment for anal fistula." Dis Colon Redtum 2002; 45;1608-15.

Athanasiadis S, Helmes C, Yazigi R, Kohler A, "The direct closure of the internal fistula opening without advancement flap for trans-sphincteric fistulas-in-ano" Dis Colon Rectum 2004; 47;1174-80.

Gustafsson U, "Excision of anal fistula with closure of the internal opening" Dis Colon Rectum 2002; 45; 1672-1678.

"Practice parameters for treatment of fistula in ano. The Standards Practice Task Force of the American Society of colon and Rectal Surgeons" Dis Colon Rectum pp. 1363-1372, Dec. 1996.

Practice parameters for treatment of fistula in ano—Supporting documentation: The Standards Practice Task Force of the American Society of Colon and Rectal Surgeons, Dis Colon Rectum, pp. 1361-1362; Dec. 1996.

Gordon N. Buchanan, M.Sc., F.R.C.S., Clive I, Bartram, F.R.C.R., Robin K.S. Phillips, M.S. F.R.C.S., Stuart W.T. Gould, M.S. F.R.C.S., Steve Halligan, M.D., F.R.C.R., Tim A. Rackall, M.D., F.R.C.S., Paul Sibbons, Ph.D., Richard G. Cohen, M.D. F.R.C.S., "Efficacy of Fibrin Sealant in the Management of Complex Anal Fistula," Dis Colon Rectum, pp. 1167-1174, Sep. 2003.

Julio Garcia-Aguilar, M.D., Ph.D., Cynthia S. Davey, M.S., Chap T. Le, Ph.D., Ann C. Lowry, M.D. and David A. Rothenberger, M.D., "Patient satisfaction after surgical treatment for fistula-in-ano," Dis Colon Rectum, pp. 1206-1212, Sep. 2000.

Schouten WR, Zimmerman DDE, Meuwissen SGM, "General Introduction and Outline of Thesis," Nederlands Tijdschrift voor Geneeskunde, Jul. 2001, 145(29); 1398-1402; https://ep.eur.nt/retrieve/2688.01.pdf#search=fistulotomy.

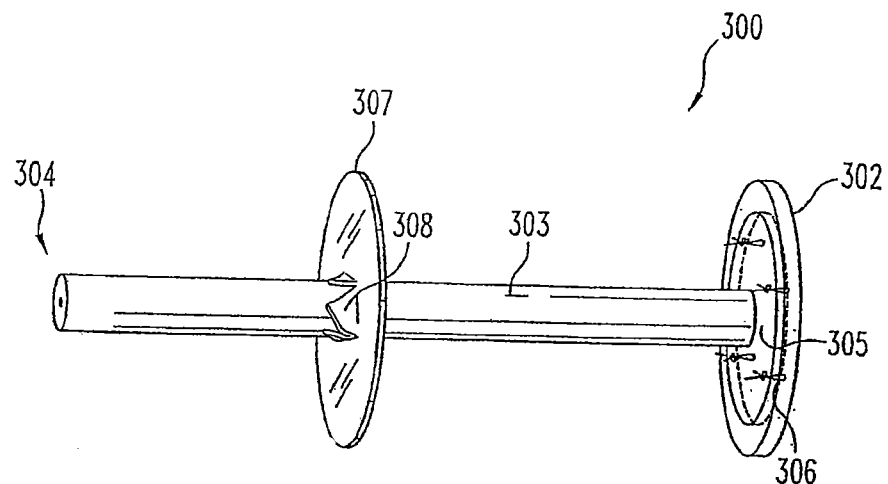
Fig. 14
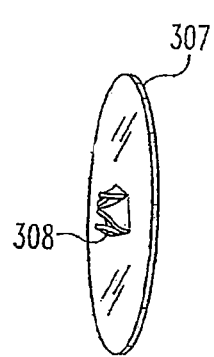 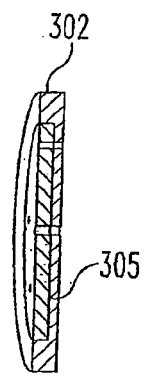
Fig. 15  Fig. 16

100
IMPLANTABLE GRAFT TO CLOSE A FISTULA

RELATED APPLICATIONS

This application is a continuation of U.S. patent application Ser. No. 11/472,642, filed Jun. 21, 2006 which claims the benefit of the filing date under 35 U.S.C. §119(e) of Provisional U.S. Patent Application Ser. No. 60/692,694, filed Jun. 21, 2005, which applications are hereby incorporated by reference.

FIELD OF THE INVENTION

The present invention relates generally to medical devices and in particular aspects to medical grafts and methods for treating fistulas.

BACKGROUND OF THE INVENTION

A variety of abnormal passages called fistulas can occur in humans. Such fistulas may be caused by, for example, an infection, a congenital defect, inflammatory bowel disease (such as Crohn's disease), irradiation, trauma, neoplasia, childbirth, or a side effect from a surgical procedure.

Some fistulas occur between the vagina and the bladder (vesico-vaginal fistulas) or between the vagina and the urethra (urethro-vaginal fistulas). These fistulas may be caused by trauma during childbirth. Traditional surgery for these types of fistulas is complex and not very successful.

Other fistulas include, but are not limited to, tracheo-esophageal fistulas, gastro-cutaneous fistulas, fistulas extending between the vascular and gastrointestinal systems, and any number of anorectal (ano-cutaneous) fistulas, such as fistulas that form between the anorectum and vagina (recto-vaginal fistulas), between the anorectum and bladder (recto-vesical fistulas), between the anorectum and urethra (recto-urethral fistulas), or between the anorectum and prostate (recto-prostatic fistulas). Anorectal fistulas can result from infection in the anal glands, which are located around the circumference of the distal anal canal forming an anatomic landmark known as the dentate line 1, shown in FIGS. 1 and 2. Approximately 20-30 such glands are found in humans. Infection in an anal gland can result in an abscess. This abscess can then track through soft tissues (e.g., through or around the sphincter muscles) into the perianal skin, where it drains either spontaneously or surgically. The resulting void through the soft tissue is known as a fistula. The internal or inner opening of the fistula, usually located at or near the dentate line, is known as the primary opening 2. The primary opening is usually the high pressure end of a fistula. Any external or outer openings, which are usually located in the perianal skin, are known as the secondary openings 3. The secondary openings are usually the low pressure end of a fistula.

FIGS. 1 and 2 show examples of the various paths that an anorectal fistula may take. These paths vary in complexity. Fistulas that take a straight line path from the primary opening 2 to the secondary opening 3 are known as simple fistulas 4. Fistula that contain multiple tracts ramifying from the primary opening 2 and have multiple secondary openings 3 are known as complex fistulas 5.

The anatomic path that an anorectal fistula takes is classified according to its relationship to the anal sphincter muscles 6, 7. The anal sphincter includes two concentric bands of muscle: the inner, or internal, sphincter 6 and the outer, or external, sphincter 7. Fistulas which pass between the two concentric anal sphincters are known as inter-sphincteric fistulas 8. Those which pass through both internal 6 and external 7 sphincters are known as trans-sphincteric fistulas 9, and those which pass above both sphincters are called supra-sphincteric fistulas 10. Fistulas resulting from Crohn's disease usually ignore these anatomic paths, and are known as extra-anatomic fistulas.

Many complex fistulas contain multiple tracts, some blind-ending 11 and others leading to multiple secondary openings 3. One of the most common and complex types of fistulas is known as a horseshoe fistula 12. In this instance, the infection starts in the anal gland (the primary opening 2) at or near the twelve o'clock location (with the patient in the prone position). From this primary opening, fistulas pass bilaterally around the anal canal, in a circumferential manner, forming a characteristic horseshoe configuration 12, as illustrated in FIG. 2. Multiple secondary openings 3 from a horseshoe fistula 12 may occur anywhere around the periphery of the anal canal, resulting in a fistula tract with a characteristic horseshoe configuration 12.

One technique for treating a fistula is to make an incision adjacent the anus until the incision contacts the fistula and then excise the fistula from the anal tissue. This surgical procedure tends to sever the fibers of the anal sphincter, and may cause incontinence.

Another technique for treating a fistula involves passing a fistula probe through the tract, in a blind manner, using primarily only tactile sensation and experience to guide the probe. Having passed the probe through the fistula tract, the overlying tissue is surgically divided. This is known as a fistulotomy. Because a variable amount of sphincter muscle is divided during the procedure, fistulotomy may result in impaired sphincter control or even incontinence. Alternative methods and instruments, such as coring-out instruments (See, e.g., U.S. Pat. Nos. 5,628,762 and 5,643,305), may make the fistula wider and more difficult to close.

Yet another technique for treating a fistula involves draining infection from the fistula tract and maturing it prior to a definitive closure or sealing procedure by inserting a narrow diameter rubber drain, known as a seton, through the tract. This is usually accomplished by inserting a fistula probe through the outer (secondary) opening 3 and gently guiding it through the fistula, and out through the inner (primary) opening 2. A seton, thread or tie is then affixed to the tip of the probe, which is then withdrawn back out of the tract, leaving the thread in place. The seton may then be tied as a loop around the contained tissue and left for several weeks or months.

An additional method of closing the primary opening is by surgically creating a flap of skin, drawing this flap of skin across the opening, and suturing the flap in place. This procedure (the endo-anal flap procedure) closes the primary opening, but is technically difficult to perform, is painful for the patient, and is associated with a high fistula recurrence rate.

More recently, methods have evolved to inject sclerosant or sealant (e.g., collagen or fibrin glue) into the tract of the fistula to block the fistula. Such sealants are described in Rhee, U.S. Pat. No. 5,752,974, for example. Usually, multiple injections are required to close the fistula by this method. In some instances, closure of a fistula using a sealant may be performed as a two-stage procedure, comprising a first-stage seton placement, followed by injection of the fibrin glue several weeks later. This procedure reduces residual infection and allows the fistula tract to "mature" prior to injecting a sealant. Injecting sealant or sclerosant into an unprepared or infected fistula as a one-stage procedure can cause a flare-up of the infection and even further abscess formation.

Even more recently, methods of treating fistulas by placing a graft in the fistula tract have been discovered, as described in co-pending application Ser. No. 11/040,996 (Armstrong), U.S. Patent Application Publication No. 2006/0074447, hereby incorporated by reference in its entirety. Such grafts may have a tapered body with a wider proximal end and a thinner distal end, as shown in FIG. 3. The graft may be pulled through the primary opening until the head portion of the graft is lodged in the primary opening, where it is retained in the same manner as a plug in a hole. The graft may also be secured by suturing the graft to the tissue of the patient, for example. Despite the tapering design of these grafts, they may still be subject to displacement or extrusion from the patient when excessive force is applied to the proximal end of the graft during exertion or straining, especially in the case of the wide fistulas that are common in patients with Crohn's disease or recto-vaginal fistulas. Although suture may be used to further secure the graft in some instances, it may be difficult to suture the proximal end of the graft to the tissues of a patient where surgical access to the primary opening of the fistula is limited, such as in anorectal and recto-vaginal fistulas where the primary opening is often located high in the rectum. Even if suturing the graft to the tissues of a patient is possible, the suturing may be painful for the patient.

Other techniques for treating fistulas are described in U.S. application Ser. No. 11/415,403, titled "VOLUMETRIC GRAFTS FOR TREATMENT OF FISTULAE AND RELATED METHODS AND SYSTEMS" (Cook Biotech Incorporated), filed May 1, 2006, which claims priority to U.S. Provisional Application Ser. No. 60/676,118, filed Apr. 29, 2005; and U.S. Provisional Application (Serial No. not yet assigned), titled "FISTULA GRAFTS AND RELATED METHODS AND SYSTEMS USEFUL FOR TREATING GASTROINTESTINAL FISTULAE" (Cook Biotech Incorporated), filed Jun. 21, 2006, naming F. Joseph Obermiller as the inventor, which are hereby incorporated by reference in their entirety.

There remains a need for improved and/or alternative medical products, methods, and systems that are useful for treating fistulas. The present invention addresses these needs.

SUMMARY OF THE INVENTION

One object of the present invention is to provide a new technique of minimally invasive fistula closure. Another object is to provide a simplified technique that obviates the need for surgical fistulotomy and avoids surgical pain and the attendant complications of the procedure. Another object of the invention is to provide an accurate and complete closure of a fistula, thereby preventing a recurrent or persistent fistula. Still another object of the invention is to provide a graft that resists unintentional displacement or expulsion and to provide methods of closing a fistula where the graft is firmly secured within the fistula. Yet another object of the invention is to provide a technique that involves no cutting or piercing of tissue, sphincter damage, or incontinence.

The present invention may be used in any type of fistula. For example, the claimed devices and methods may be used to graft or occlude tracheo-esophageal fistulas, gastro-cutaneous fistulas, anorectal fistulas, fistulas occurring between the vagina and the urethra or bladder, fistulas occuring between the vascular and gastrointestinal systems, or any other type of fistula.

The present invention provides grafts and methods designed to simplify implantation of a graft in a fistula of a patient and to resist expulsion of the graft from the patient during exercise or straining. The graft of the present invention may have a generally conical graft body having a wider proximal end that tapers to a narrower distal end, a generally cylindrical graft body, a sheet form graft body, or a graft body having any other shape suitable for implantation within a fistula. The graft body or any portion of the graft body may have passages therethrough and may have a central lumen for placement of a guidewire.

The graft of the present invention may include a cap in the form of a disc, cone, sphere, hemisphere, trumpet-shape, polygon, or any other suitable shape. Desirably, the cap extends laterally from the head portion of the graft body and prevents migration of the graft and/or extrusion of the graft from the fistula. The cap may be integral with the body of the graft or may be a separate structure that is attachable to the body of the graft in a non-permanent manner. The cap may be moveable along the body of the graft or secured to the graft body using any suitable method. For example, absorbable sutures may be passed through apertures in the cap to secure the cap to the graft body. In some embodiments of the invention, after the sutures dissolve and sufficient time elapses for the graft to become firmly secured within the fistula tract (e.g. by incorporation of host tissue into the graft), the cap detaches from the graft and is released into the body.

The graft may also include an elongated tail extending from the end of the graft body opposite the end on which the cap is located. Such a tail facilitates implantation of the graft within a fistula and eliminates the need for an initial seton placement step.

In another embodiment of the graft of the present invention, a second cap is used to secure the end of the graft body opposite a first cap. The first cap may be used to prevent dislodgement of the graft in one direction, and the second cap may be used to prevent dislodgement of the graft in the opposite direction. In some embodiments, suture may be passed through apertures in the first cap, through the body of the graft, and then through apertures in the second cap, thereby securing the caps to the graft body.

The graft of the present invention may be made of any suitable biological or synthetic material. Desirably, the material elicits little immunological reaction, has some inherent resistance to infection, and promotes tissue reconstruction (rather than complete absorption of the graft into the surrounding tissue), thereby occluding the fistula. The graft may also incorporate one or more bioactive agents.

In certain embodiments of the present invention, the graft is made of a material receptive to tissue ingrowth. In such aspects, upon deployment of the product in accordance with the present invention, cells from the patient can infiltrate the material, leading to new tissue growth on, around, and/or within the graft. In some embodiments, the graft comprises a remodelable material, such as small intestinal submucosa (SIS). In these embodiments, the material promotes and/or facilitates the formation of new tissue, and is capable of being broken down and replaced by new tissue in such a way that the original fistula closure achieved by the implanted graft product is maintained throughout the remodeling process so as to eventually form a closure or substantial closure with the new tissue.

The present invention also provides methods of treating fistula. In one embodiment of the method of the present invention, a graft having a graft body, a cap that is integral with or detachable from the graft body, and an elongated tail is inserted into the fistula tract until the cap abuts the primary opening of the fistula, the graft body extends into at least a portion of the fistula tract, and the tail protrudes from the secondary opening of the fistula. The cap may include a plurality of holes, such as those in a button, so that, absorbable suture can be inserted through the holes and used to secure the cap to the graft body. The tail of the graft may be secured in place by any suitable means of affixation, such as by suturing the tail to the tissues of the patient or by using a securing device, such as a second cap or a bead with a central lumen, through which the tail may be passed and secured by crimping or suturing, thereby eliminating the need to place sutures in the tissues of the patient and the corresponding discomfort to the patient. Any excess portions of the tail and/or graft may then be trimmed. The cap maintains the graft body in the fistula tract and prevents it from being displaced or extruded during exertion or straining by the patient. After a period of time, the absorbable suture attaching the cap(s) to the graft body dissolves, allowing the cap(s) to fall off and be passed out of the body. By this time the graft is firmly secured within the fistula tract.

Additional features and advantages of the present invention will be apparent to one of ordinary skill in the art from the drawings and detailed description of the preferred embodiments below.

BRIEF DESCRIPTION OF THE DRAWINGS

FIG. 14 shows still another embodiment of the graft of the present invention having one cap attached to an end of the graft body and another cap that is configured to slide along the graft body.

FIG. 15 shows the slideable cap of FIG. 14.

FIG. 16 shows the cap that is attached to one end of the graft body of FIG. 14.

DETAILED DESCRIPTION OF THE PREFERRED EMBODIMENT

Figure 1:
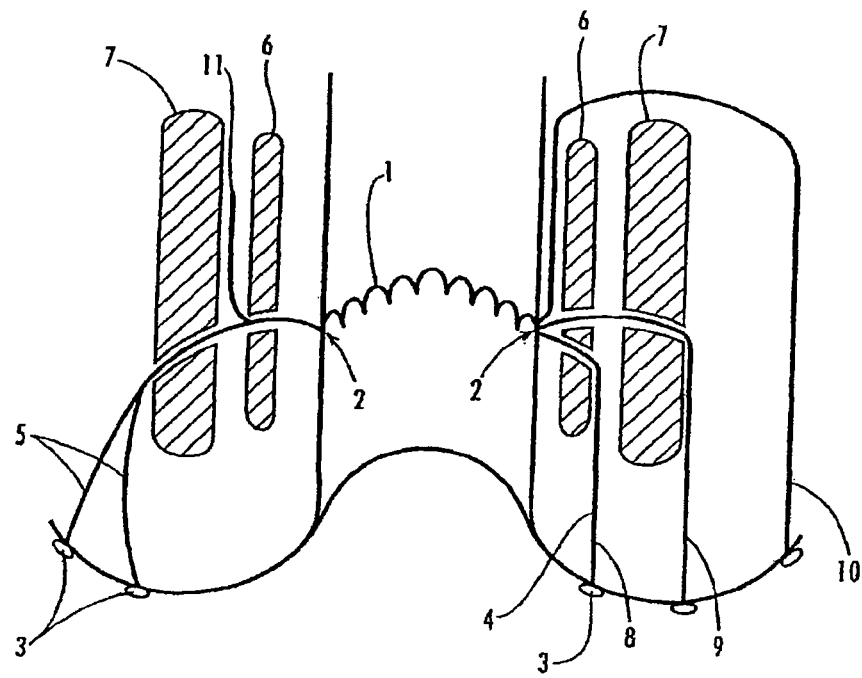
FIG. 1 shows several possible anatomic courses taken by various forms of anorectal fistula (longitudinal plane)

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

Turning now to a discussion of the particular grafts, systems, and methods of the present invention useful for treating fistulas, illustrative grafts of the invention are configured to block at least the primary opening of a fistula, i.e., the primary opening and potentially one or more other segments of a fistula, for example, the fistula tract and/or any secondary openings. In this context, the term "fistula tract" is meant to include, but is not limited to, a void in the soft tissues extending from a primary fistula opening, whether blind-ending or leading to one or more secondary fistula openings. Also, as used herein, the terms "graft" and "plug" may be used interchangeably.

Figure 2:
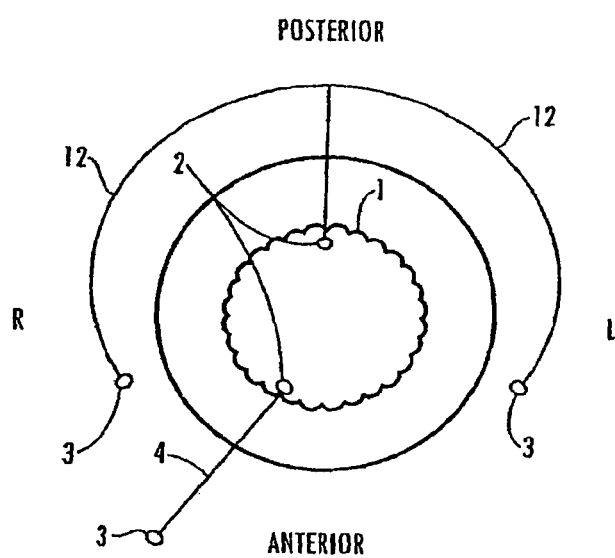
FIG. 2 shows a perineal view of a simple anorectal fistula and a horseshoe fistula.

The graft of the present invention may be used to graft or occlude any type of fistula, such as the types of anorectal fistula illustrated in FIGS. 1 and 2. Other types of fistula that may be occluded by the present invention include, but are not limited to, tracheo-esophageal fistulas, gastro-cutaneous fistulas, or fistulas occurring between the vagina and bladder (vesico-vaginal fistulas), between the vagina and urethra (urethro-vaginal fistulas), between the anorectum and vagina (recto-vaginal fistulas), between the anorectum and bladder (recto-vesical fistulas), between the anorectum and urethra (recto-urethral fistulas), between the anorectum and prostate (recto-prostatic fistulas), or between the vascular and gastrointestinal systems.

In certain embodiments, the graft of the present invention includes a cap and an elongate graft body extending from the cap, where the cap is configured to contact portions of the alimentary canal wall adjacent to the primary opening, and the graft body is configured to extend into at least a portion of the fistula tract. In other embodiments, the graft of the present invention includes a second cap configured to contact portions of the tissue adjacent to the secondary opening. In still other embodiments, the graft of the present invention also includes an elongated tail, which may be used to eliminate the need for a separate seton placement step in the implantation procedure. The graft body preferably comprises a remodelable material, for example, a remodelable extracellular matrix material (ECM) such as submucosa. The invention also provides methods utilizing such a graft and medical products that include such a graft enclosed within sterile packaging.

Figure 4:
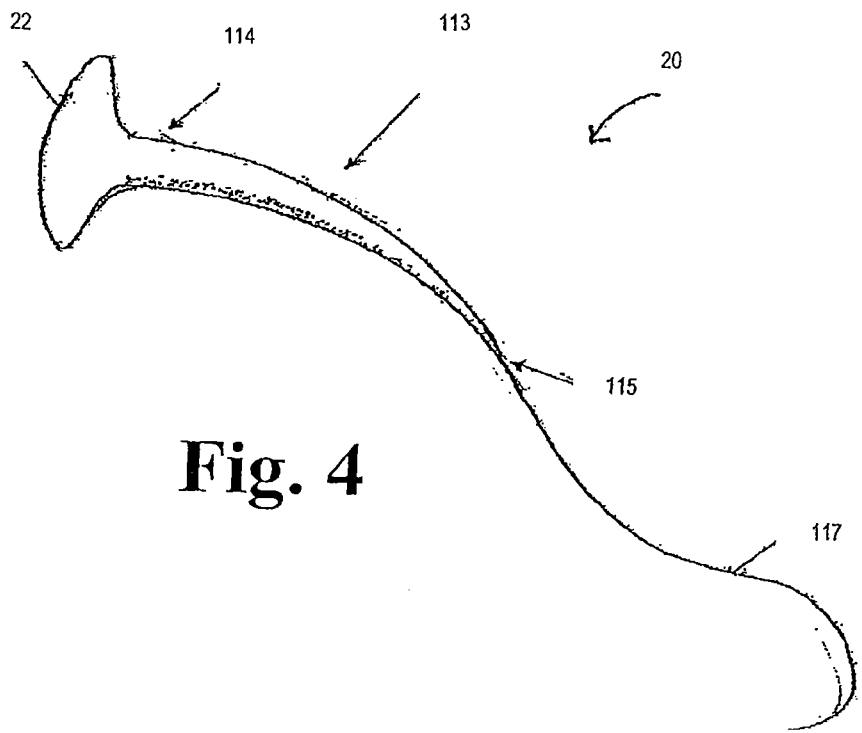
FIG. 4 shows one embodiment of the graft of the present invention having a generally conical graft body with an integral cap and an elongated tail.

With reference now to FIG. 4, one embodiment of the biocompatible graft 20 of the present invention includes a graft body 113 having a proximal end 114 and a distal end 115, a cap 22, and a tail 117. The graft body may have any suitable configuration. For example, the graft body may have a configuration that is generally convex, concave, S-shaped, straight, curved, flat, polygonal, conical, cylindrical, elliptical, or hemispherical, or it may have any other configuration capable of being inserted into and secured within a fistula. In some embodiments, the graft body is curved to conform to the shape of the fistula, thereby facilitating introduction of the graft, a secure fit of the graft within the fistula, and less discomfort for the patient.

Figure 3:
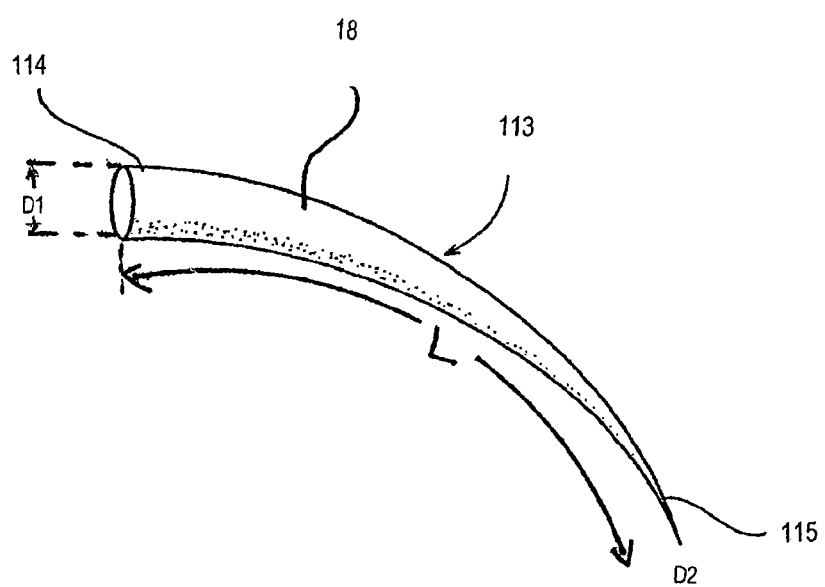
FIG. 3 shows one embodiment of the graft body of the present invention.
Figure 5:
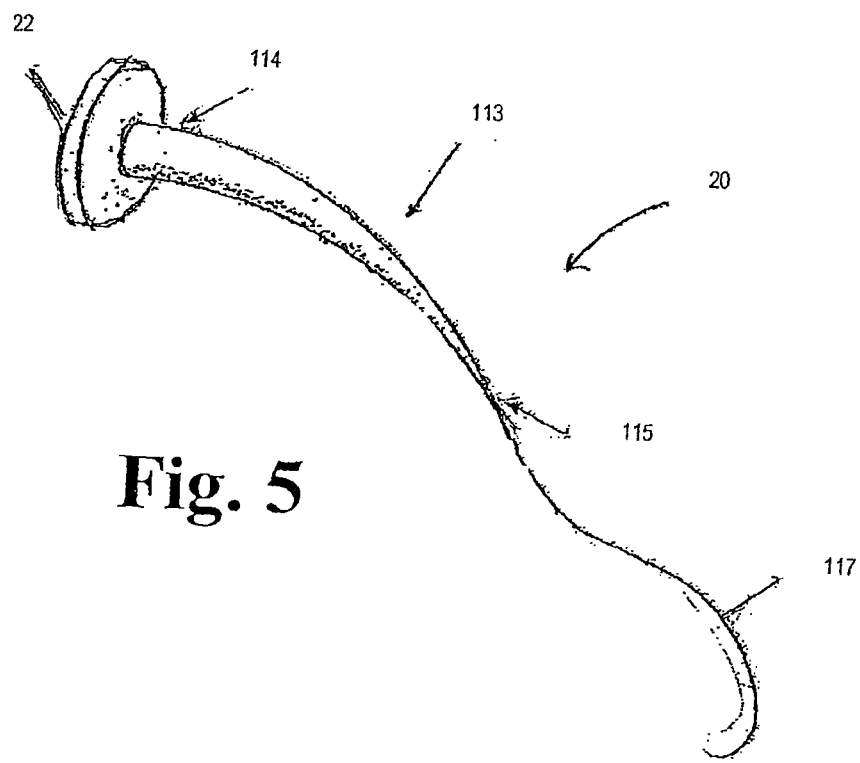
FIG. 5 shows another embodiment of the graft of the present invention having a generally conical graft body with an attachable cap and an elongated tail.
Figure 11:
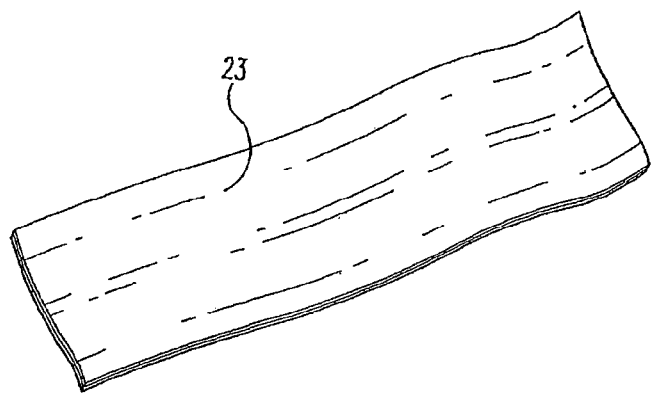
FIG. 11 is a perspective view of an illustrative sheet form graft body of the present invention.

In the embodiments shown in FIGS. 3, 4, and 5, the graft body 113 has a generally conical configuration that continuously tapers from a thicker trumpet-shaped proximal end 114 having a first diameter D1 to a thin filamentous distal end 115 having a second diameter D2, where the first diameter D1 is greater than the second diameter D2. The degree of taper may vary depending on a number of factors, including but not limited to, the diameter of each of the ends (D1 and D2) and the length L of the graft. In other embodiments, the graft has a generally cylindrical body or a body in the form of a sheet, for example, as shown in FIGS. 6-8 and 11. Although the sheet form material depicted in FIG. 11 is generally in the shape of a rectangle, the graft body of the present invention, in certain aspects, can include sheet form material exhibiting any suitable rectilinear or curvilinear shape, for example, an isosceles triangle or any other suitable triangular or triangular-like shape, just to give a few non-limiting examples).

In some embodiments, a graft body is formed by folding or rolling, or otherwise overlaying one or more portions of a biocompatible material, such as a biocompatible sheet material, as described in U.S. Provisional Application Ser. No. 60/763,521, titled "FISTULA GRAFTS AND RELATED METHODS AND SYSTEMS FOR TREATING FISTULAE" (Cook Biotech Incorporated), filed Jan. 31, 2006, which is hereby incorporated by reference in its entirety. In certain embodiments, the overlaid biocompatible sheet material can be compressed and dried or otherwise bonded into a volumetric shape such that a substantially unitary construct is formed. Such a substantially unitary graft body can then be placed in a fistula in a manner such that a cap contacts portions of the alimentary canal wall adjacent to the primary opening, and the graft body extends into at least a portion of the fistula tract (and potentially fills the primary fistula opening, the fistula tract, and/or any secondary fistula openings, or any portions thereof). The size of the cross section of the graft body is generally constant along the length of the graft. In some embodiments, the graft body is configured so that its cross section increases in size moving toward the cap. Such a configuration can provide a more snug fit of the graft at or near the primary opening upon implantation. In some embodiments, the graft body has portions that are tapered and/or curvilinear.

The graft body of the present invention may have any dimensions suitable for implantation within a fistula. The graft body will be of sufficient size and shape to extend into at least a portion of a fistula tract, and will generally (but not necessarily) be of sufficient dimension to fill a fistula, or a segment thereof, e.g., the primary fistula opening, a fistula tract, and/or any secondary fistula openings, either alone or in combination with other similar or differing medical devices.

In certain embodiments having a tapered, generally conical shape, such as the embodiments shown in FIGS. 3, 4, and 5, it is desirable for the graft body to have a length L of about 1 to about 15 centimeters, a first diameter D1 of about 1 to about 20 millimeters, and a second diameter D2 of about 0.1 to about 5 millimeters. More desirably, the generally conical graft body has a length L of about 3 to about 12 centimeters, a first diameter D1 of about 2 to about 15 millimeters, and a second diameter D2 of about 0.5 to about 3.5 millimeters; and even more desirably, the graft body has a length L of about 5 to about 10 centimeters, a first diameter D1 of about 5 to about 10 millimeters, and a second diameter D2 of about 1 to about 2 millimeters. The taper may or may not be continuous along the length of the graft body.

As another example, in certain embodiments having a generally cylindrical graft body, such as the embodiments shown in FIGS. 6-8 and 12-14, it is desirable for the graft body to have a length of at least about 0.2 centimeters, and in many situations at least about 1 to about 20 centimeters. In illustrative embodiments, the graft body has a length of from about 2 to about 5 centimeters, or alternatively, from about 5 to about 10 centimeters. Additionally, in certain embodiments, the graft body will have a diameter, which may or may not be constant along the length of the graft body, of from about 0.1 to about 25 millimeters, or more typically from about 5 to about 10 millimeters. The graft of the present invention may be used to close any diameter of primary opening up to the limits of the diameter of the proximal end of the graft body.

In certain embodiments having a generally flat, sheet form graft body, such as the embodiment shown in FIG. 11, the size of the graft body for a particular treatment application will be based, at least in part, on the general size and shape of the fistula being treated. A sheet form graft body may be sized such that the diameter of the primary opening is less than the width of the sheet so that as the sheet is drawn into the fistula tract, it is forced to fold and/or roll over itself one or more times to conform to soft tissues surrounding the fistula, and is gradually "wedged" into the primary opening, and potentially at least a portion of the fistula tract and/or any secondary openings of the fistula, so as to block these spaces when sufficiently pulled therethrough. Such lodging in place may be sufficient to obviate the need for otherwise securing the graft to the soft tissues at or near the primary opening, fistula tract, and/or any secondary openings. Nonetheless, in certain aspects, the graft is further secured to such soft tissues, for example, by suturing.

In certain embodiments of the present invention, the graft includes an anchoring adaptation to maintain the graft body within the fistula tract and/or to maintain the cap in place following implantation of the graft. For example, the graft may have protrusions on its outer surface, such as the protrusions 18 shown in FIG. 3, to assist in anchoring the graft within the fistula. Other suitable anchoring adaptations include but are not limited to barbs, hooks, sutures, adhesives, ribs, and the like. Such anchoring adaptations, while advantageous in certain embodiments of the invention, are not necessary to broader aspects of the invention. Illustratively, certain grafts are configured so that a cap is used to maintain contact with portions of the alimentary canal wall adjacent to the primary opening following implantation without the need for such anchoring adaptations. Such a cap may assist in preventing the graft body from being displaced or extruded from the fistula tract in a manner similar to a head on a nail, which prevents the elongated portion of the nail from being moved in a direction opposite the head. In other embodiments of the invention, suitable anchoring adaptations may aid or facilitate the maintenance of such contact.

The use of a cap on one or both ends of the graft body may to prevent migration or displacement of the graft body or extrusion of the graft body from the fistula tract allows the use of a variety of different types of graft bodies. The use of a tapered graft body having a proximal end that is adapted to be wedged into the fistula tract, although used in some embodiments of the invention, is not necessary to properly secure a graft within the fistula tract when the graft includes a cap on its proximal end. Although such a tapered design may still be used in conjunction with a cap, other simpler and less expensive graft bodies may be used instead of a tapered design, without sacrificing the mechanical stability of the graft within the fistula tract.

The cap of the present invention may be of any suitable shape and configuration and may include any suitable device and/or material for contacting portions of the alimentary canal wall adjacent to the primary opening, and/or for contacting any secondary openings of the fistula tract. Illustratively, the cap can include one or more objects (e.g., pieces of material or discrete shapes) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof. Suitable three-dimensional curvilinear bodies can include, for example, spheres, spheroids, ellipsoids, cylinders, cones, and any suitable variations thereof (e.g., a segment of a sphere, or a truncated cone, etc.). Additional cap shapes and configurations can include, for example, a disc, a sphere, a hemisphere, a convex or concave form, a cone, a ring, a spring, a mesh, a lattice, a cylinder, an umbrella, a coil, a prong, a polygon, a flaring (trumpet-shaped) form, or any other suitable shape or form that extends laterally beyond the circumference of the graft body. Caps useful in the invention can be prepared, for example, as described in U.S. Provisional Application Ser. No. 60/763,521, titled "FISTULA GRAFTS AND RELATED METHODS AND SYSTEMS FOR TREATING FISTULAE" (Cook Biotech Incorporated), filed Jan. 31, 2006, which is hereby incorporated by reference in its entirety.

Any cap present in an embodiment of the present invention (e.g., a cap to be positioned at a rectal wall fistula opening and/or a cap to be positioned at a vaginal wall fistula opening) may be constructed along with the elongate graft body to provide a single unitary construct, for example, a single- or double-capped device formed from a single piece of material or other substance. In some embodiments, a particular cap may be formed separately from an elongate graft body and then subsequently combined or otherwise retained in association with the graft body, for example, by suturing the two together, applying an adhesive, using mechanical fastener(s), or employing any other suitable means or combination thereof. In one embodiment, the graft comprises an elongate graft body and two caps, wherein the caps are formed separately from the graft body and are attached to opposite ends of the graft body, e.g., before or during an implantation procedure.

In some forms, one or more caps are each formed separately from the graft body, and then coupled to the graft body with an absorbable device or material. These coupling elements can exhibit any suitable size, shape, and configuration, and in some embodiments, take the form of an adhesive or one or more hooks, fasteners, barbs, straps, suture strands, or combinations thereof. Additionally, such devices and materials can be configured to degrade at varying rates upon being implanted in vivo. In one embodiment, 2-0 vicryl suture material is used to join one or more caps to an elongate graft body. Illustratively, a coupling element can be adapted to desirably hold one or more caps in association with a graft body during product handling and implantation, and then upon implantation, to degrade at a desirable rate. In some modes of operation, a cap and an elongate graft body, at least due in part to degradation of the coupling element, can uncouple or otherwise disengage from one another after a period of time following implantation, allowing the cap to pass through and out of the body naturally. For caps to be positioned on the rectal-side of a recto-vaginal fistula, for example, this decoupling can be facilitated and/or promoted by naturally occurring forces generated during peristalsis.

When formed separately, a cap may or may not be comprised of the same biocompatible material(s) as the elongate graft body (or, if present, another cap). In certain aspects, the elongate graft body and/or any cap present are comprised of a remodelable material, and in some embodiments, a remodelable collagenous material. Illustratively, a cap and an elongate graft body can be formed from separate pieces of remodelable, collagenous material (e.g., remodelable SIS material), and thereafter coupled to one another in accordance with the present invention. In one embodiment, a cap attached to one end of a graft body comprises a synthetic material (e.g., Nylon), while a cap attached to the opposite end of the graft body comprises a naturally-derived material (e.g., an ECM material such as porcine SIS). In some embodiments, the use of a cap on one or both ends of the graft body serves to protect the graft body during remodeling, e.g. by protecting the remodelable graft body from the fluids or other contents within the mammalian body or from substances in the external environment near the primary and/or secondary openings of the fistula.

The components of an inventive graft construct (e.g., a graft body, tail, and/or one or more caps), whether formed separately or together as a single unit, can be constructed in any suitable manner, for example, using any of the processes described herein. In some embodiments, a graft body, tail, and/or one or more caps are formed with a reconstituted or otherwise reassembled ECM material. Graft bodies, tails, and/or caps can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive graft component is constructed by randomly or regularly packing one or more pieces of single or multilayer ECM sheet material within a mold and thereafter processing the packed material. Elongate graft bodies useful in the invention can be prepared, for example, as described in U.S. application Ser. No. 11/415,403, titled "VOLUMETRIC GRAFTS FOR TREATMENT OF FISTULAE AND RELATED METHODS AND SYSTEMS" (Cook Biotech Incorporated) filed May 1, 2006, which claims priority to U.S. Provisional Application Ser. No. 60/676,118, filed Apr. 29, 2005, which is incorporated by reference in its entirety.

When implanted in accordance with certain embodiments of the present invention, and contacting portions of the tissues adjacent to a primary opening, the cap may or may not have a portion extending into the primary opening. For example, in some aspects, the graft body is configured so that no portion of the cap resides within the primary opening when the graft body is implanted, while in other aspects, the graft is configured so that a portion of the cap does reside within the primary opening when the graft is implanted. It is the graft as a whole, e.g., the combination of the cap and the graft body, that is configured to block at least the primary opening of a fistula. However, neither the cap nor the graft body need be configured to block the primary fistula opening independent of the other member, although either member may be so configured. Additionally, the cap, by itself, may or may not be configured to block the fistula tract. In this regard, blocking a particular space or void can be accomplished by filling that space with the cap, or a portion thereof. In certain aspects, the cap can be configured to fill the primary opening, the fistula tract (or any portion thereof), and/or any secondary openings of the fistula. Such filling can, in some embodiments, seal off or substantially seal off the primary opening, the fistula tract (or any portion thereof), and/or any secondary openings of the fistula.

When suitably implanted, and thus extending into at least a portion of the fistula tract, the graft body may or may not have a portion extending into the primary opening. For example, in some aspects, the graft is configured so that at least a portion of the graft body resides within the fistula tract but no portion of the graft body resides within the primary opening when the graft is implanted. In other aspects, the graft body is configured to extend through the primary opening and into at least a portion of the fistula tract when the graft body is implanted. Again, it is the graft as a whole, e.g., the combination of the cap and the graft body, that is configured to block at least the primary opening of a fistula. Additionally, the graft body, by itself, may or may not be configured to block the fistula tract. Further, the graft body, by itself, may or may not be configured to block any secondary fistula opening. In this regard, blocking a particular space or void can be accomplished by filling that space with the graft body, or a portion thereof. In certain embodiments, the graft body can be configured to fill the primary opening, the fistula tract (or any portion thereof), and/or any secondary openings of the fistula. Such filling can, in some embodiments, seal off or substantially seal off the primary opening, the fistula tract (or any portion thereof), and/or any secondary openings of the fistula.

With reference now to FIG. 4, one embodiment of the cap is a flaring, or trumpet-shaped cap 22, which projects laterally beyond the circumference of the proximal end 114 of the graft body 113. The cap 22 in this embodiment is integral with the graft body 113.

With reference now to FIG. 5, another embodiment of the cap 22 is a disc-shaped structure that is attachable to the proximal end 114 of the graft body 113. In certain embodiments, the transverse profile of the disc may be oblong, convex, concave or any suitable combination thereof, for example. The means of affixing an attachable cap to a graft body may be permanent or non-permanent. Where the device is affixed in a non-permanent manner, such as by absorbable sutures, the cap detaches from the graft body after a certain period of time, by which time the graft body desirably has become ingrown into the fistula tract (e.g., as a result of the use of a graft material that supports the ingrowth of host tissue). The timing of the release of the cap may vary, depending upon the thickness and dissolution characteristics of the material used for attaching the cap to the graft body. Desirably, the length of time elapsed before the cap detaches is about 1 to about 8 weeks, more desirably about 2 to about 6 weeks, and even more desirably about 4 weeks.

The cap used in the graft of the present invention may have any suitable dimension. The suitable dimensions will depend upon several factors, including but not limited to, the size of the primary and/or secondary openings of the fistula tract and the size of the graft body. Desirably, the diameter (or other lateral dimension) of the cap is larger than the diameter (or width) of the graft body and larger than the diameter of the opening of the fistula tract that will be adjacent to the cap when the graft is implanted. As one example, the disc-shaped cap shown in FIGS. 5 and 6 desirably has a diameter of about 0.2 to about 5 centimeters. More desirably, the diameter of the cap is about 0.5 to about 2 centimeters, and even more desirably, the diameter is about 1 centimeter. Desirably, the cap has a thickness of about 0.01 to about 1 centimeter. More desirably, the cap has a thickness of about 0.05 to about 0.5 centimeters, and even more desirably the thickness is about 0.1 to about 0.3 centimeters.

The cap may be composed of any biocompatible absorbable or non-absorbable material. The cap may be made of the same material as the remainder of the graft body. Examples of such materials are described in detail herein. Alternatively, the cap may be composed of a biocompatible material that differs from the material of the remainder of the graft body. In some embodiments, the cap is made of a hydrocarbon, plastic, or polymer material. In other embodiments, the cap is made of a suitable absorbable material such as an extracellular matrix material, which allows the cap to become incorporated into the adjacent tissue, rather than becoming detached from the graft body.

In some embodiments of the present invention, the graft includes an elongated tail 117, as shown in FIGS. 4 and 5. Such a tail 117 may be attached to a probe and used to avoid the initial step of inserting a seton, thread or tie into the fistula tract before implanting a graft. Desirably, the tail 117 is about 5 to about 50 centimeters long. More desirably, the tail is about 10 to about 40 centimeters long. Even more desirably, the tail is about 20 to about 30 centimeters long. The diameter of the tail is desirably about 0.01 to about 1 millimeter, more desirably about 0.1 to about 0.5 millimeters, and even more desirably about 0.2 to about 0.3 millimeters. The tail may be made of any suitable material, as described herein, and may or may not be made of the same material as the remainder of the graft.

The cap, graft body, and/or tail of the present invention may be formed as an integral unit (e.g., from a single piece of biocompatible material), or alternatively, any component(s) of the graft may be formed separately and then combined together, for example, using an adhesive, sutures, mechanical fastener(s), and/or any other suitable joining means. When formed separately, the graft components may or may not be comprised of the same biocompatible material(s). In certain preferred aspects, the components are comprised of a remodelable material such as a remodelable extracellular matrix material. Illustratively, the components can be formed from separate pieces of remodelable SIS material, and thereafter coupled to one another to form the graft. However, it should be noted that, in certain aspects, the components are formed from separate pieces of material, yet are retained in association with one another without the use of any other device or material (e.g., sutures, an adhesive, etc.). For example, the cap(s) and the graft body may be held together by having at least one member (or any portion thereof) received around, through, over, etc., the other member (or any portion thereof). The components of the present invention, whether formed separately or together as a single unit, can be constructed in any suitable manner, for example, using any of the processes described herein. In some embodiments, the components are formed with a reconstituted or otherwise reassembled ECM material.

Figure 6:
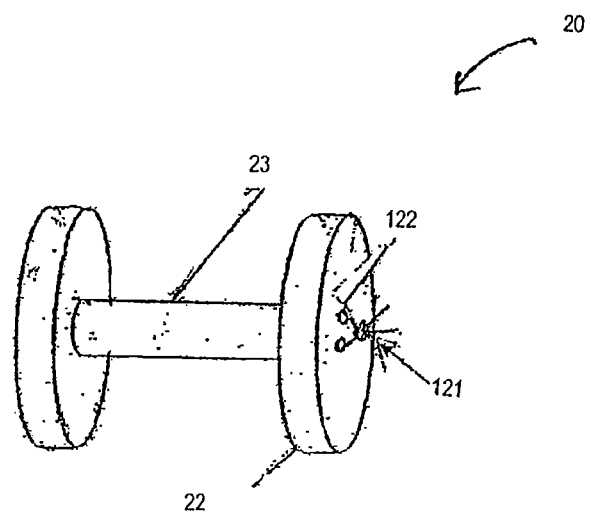
FIG. 6 shows still another embodiment of the graft of the present invention having a generally cylindrical body with two attachable caps.

With reference now to FIG. 6, one embodiment of the graft of the present invention has a generally cylindrical graft body 23, which is secured at each end of the fistula tract by means of a "button" shaped cap 22. These caps 22 may be affixed to the graft body by any suitable means, such as by absorbable sutures 121 passed through a plurality of apertures 122 in the caps 22, in a manner similar to stitching a button to a shirt. Alternatively, the graft may incorporate an integral cap that extends laterally from one end of the graft body 23 and assists in preventing dislodgement of the graft from the fistula tract. A second cap or other means of securement may be used to secure the other end of the graft body and to assist in preventing dislodgement of the graft in the opposite direction.

Figure 7:
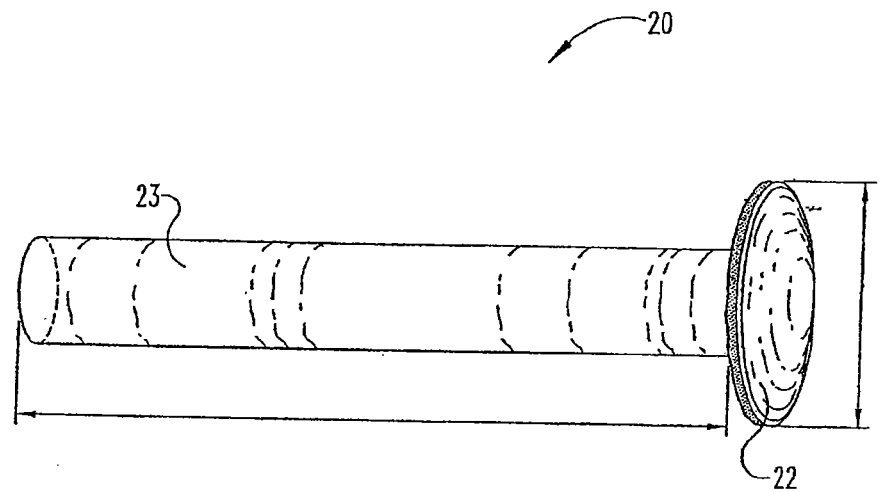
FIG. 7 is a perspective view of an another embodiment of the graft of the present invention.

With reference now to FIG. 7, in one embodiment of the graft of the present invention, a cylindrical graft body 23 extends from a cap 22 that is generally in the shape of a disk. The cap 22, which may be made of an extracellular matrix material (e.g., SIS), may be configured to contact portions of the alimentary canal wall adjacent to the primary opening. The graft body 23, which may also be made of an extracellular matrix material, is generally cylindrical and is configured to extend into at least a portion of the fistula tract. The graft body 23 may or may not be sized and shaped to fill the entire fistula tract.

Figure 8:
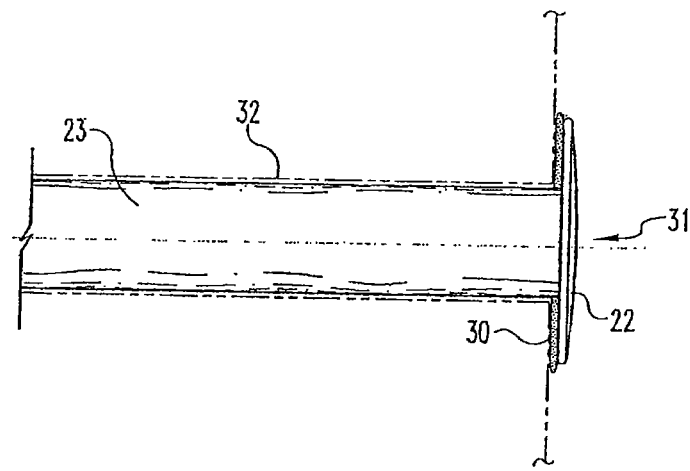
FIG. 8 is a side view of the graft of FIG. 7 implanted within a patient.

With reference now to FIG. 8, an illustrative manner of using the graft 20 of FIG. 7 to treat a patient is shown. As depicted, the graft 20 can be implanted within a patient so that the cap 22 contacts portions of the alimentary canal wall 30 adjacent to the primary opening 31, and the graft body 23 extends into at least a portion of the fistula tract 32.

Figure 9:
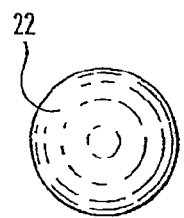
FIG. 9 is a perspective view of an illustrative cap of the present invention.

With reference now to FIG. 9, shown is an alternative cap 22, which is generally in the shape of a bead. This illustrative cap can be coupled to or otherwise joined with any graft body described herein (e.g., the graft body depicted in FIG. 11, as one non-limiting example). This cap may be comprised of an absorbable material, and generally sized and adapted to suitably contact portions of the tissues surrounding the primary and/or secondary openings of a fistula tract.

Figure 10A:
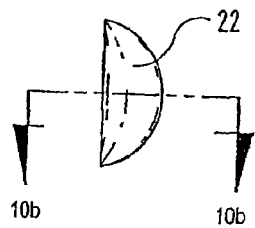
FIG. 10A is a side view of another illustrative cap of the present invention.
Figure 10B:
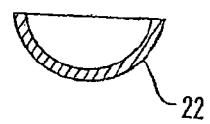
FIG. 10B is a cross sectional view of the cap of FIG. 10A along the view line 10b-10b shown in FIG. 10A

FIG. 10A shows a side view of another alternative cap 22 of the present invention. FIG. 10B shows a cross sectional view of the cap of FIG. 10A along the line 10b-10b. The shape of this cap 22 generally resembles the shape of a lens or bowl. Such a cap may or may not have a hollow portion. This cap can be coupled to or otherwise joined with any graft body described herein, and the cap and graft body can be joined in any suitable manner and in any suitable configuration relative to one another, for example, so that peripheral regions of either the top or bottom face of the cap contacts portions of the alimentary canal wall adjacent to the primary opening and/or portions of the tissues adjacent to the secondary opening.

With reference now to FIG. 11, shown is a perspective view of another illustrative graft body 23 of the present invention. This graft body 23 comprises a compliant sheet form biocompatible material comprising two layers of extracellular matrix material bonded together. This sheet form graft body can be coupled to or otherwise joined with any of the caps described herein, for example, the disk-shaped cap of FIG. 7 or the bead-shaped cap of FIG. 9, just to name a few. This sheet form graft body can be prepared, for example, as described in U.S. application Ser. No. 11/414,682, titled "FISTULA GRAFT WITH DEFORMABLE SHEET FORM MATERIAL" (Cook Incorporated), filed on Apr. 28, 2006, which claims priority to U.S. Provisional Application Ser. No. 60/676,482, filed Apr. 29, 2005, which are hereby incorporated by reference in their entirety.

The sheet form material is deformable upon impingement by soft tissue surrounding a fistula (e.g., tissue surrounding the primary fistula opening, the fistula tract, and/or any secondary fistula openings). Such deformable materials can include any of the extracellular matrix or other biocompatible materials described herein, for example, a multilaminate sheet of remodelable SIS material. Further, the sheet form graft is sized and shaped so as to be deformable to a three-dimensional volumetric body extending into at least a portion of the fistula tract, and potentially filling at least a portion of the fistula tract, the primary opening, and/or any secondary openings of the fistula. In so doing, advantageous implant materials will also be sufficiently flaccid to avoid substantial cutting or tearing of the surrounding soft tissues.

In some embodiments of the present invention, the inventive grafts are useful in treating recto-vaginal fistulas. Illustratively, such grafts can be configured to block at least a fistula opening occurring in a rectal cavity wall, i.e., a rectal-side opening and potentially one or more other segments of a recto-vaginal fistula, for example, a fistula tract and/or any openings occurring in a vaginal cavity wall. In advantageous embodiments, these products will at least include a cap and an elongate graft body extending from the cap, where the cap is configured to contact portions of the rectal cavity wall adjacent to the fistula opening, and the elongate graft body is configured to extend into, and in some cases fill, at least a portion of a recto-vaginal fistula tract. Some of these products will additionally include a second cap to be positioned in and/or around a vaginal wall fistula opening. While these products are particularly suited for treating recto-vaginal fistulae, it will be understood that such products may be useful in treating other types of fistulae as well, and in some forms, are useful in filling, blocking or otherwise treating non-fistula openings or passages occurring in the body.

The grafts of the present invention and their components can exhibit any suitable size and shape for treating recto-vaginal fistulae and other bodily openings and passageways. A graft body may either have a constant or varying cross-sectional area along its length. Also, as discussed in more detail below, some graft bodies of the invention can have one or more lumens extending at least partially through the bodies along their length.

Figure 12:
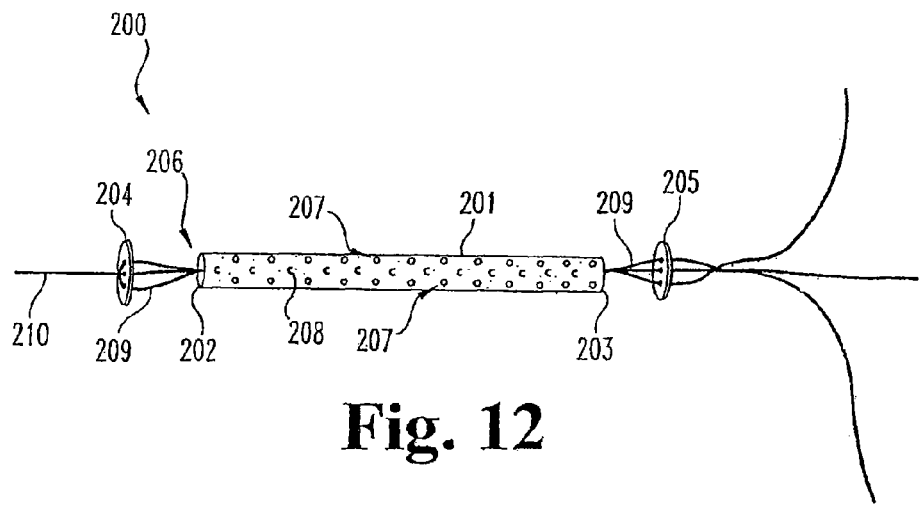
FIG. 12 shows one embodiment of the graft of the present invention having two caps connected to the graft body with suture.

Referring now to FIG. 12, shown is a fistula plug 200 which is useful in treating recto-vaginal fistulae. Fistula plug 200 is comprised of an elongate plug body 201 having a first end 202 and a second end 203. Fistula plug 200 also includes a first cap 204 and a second cap 205, both of which are generally disk-shaped and have multiple apertures formed therein. Plug body 201, which is generally in the shape of a cylinder, is sized and adapted for placement in a fistula tract, and in some forms, is configured for filling at least a portion of a fistula tract. Plug body 201 can be formed with any suitable biocompatible material, and in some embodiments, comprises a collagen-containing material such as a remodelable ECM material. Plug body 201 has a central lumen 206 extending through the construct along its length. Lumen 206, inter alia, can enable plug body 201 to be deployed over an emplaced guidewire or other similar device. Additionally, there are multiple rows of passages 207 occurring in plug body 201. These longitudinal rows are spaced evenly apart and staggered, and the passages 207 in each row are equidistant from one another along the length of plug body 201. The longitudinal axis of each passage runs through (and perpendicular to the longitudinal axis of) central lumen 206 to allow communication between opposing sides of the exterior surface of plug body 201. Plug body 201 also has multiple surface protuberances 208 extending out from its exterior surface.

As depicted in FIG. 12, the first cap 204 and second cap 205 are initially detached from elongate plug body 201, but are retained in association with plug body 201 by suture strand 209, which passes through plug body lumen 206, through and around the first cap 204, and through second cap 205. In this configuration, suture strand 209 can be manipulated in such a fashion that the first cap 204 and second cap 205 are brought in contact with first plug body end 202 and second plug body end 203, respectively. For example, the ends of suture strand 209 can be pulled tight, and portions of suture strand 209 can be secured together (e.g., knotted together) so that the two caps remain in contact with the ends of plug body 201. Additionally or alternatively, the first cap 204 and/or second cap 205 can be sutured or otherwise coupled or bonded to plug body 201. Depending on the particular application, bringing a cap in contact with a plug body end (and potentially also securing the cap to the plug body end) can occur before or during an implantation procedure. For example, a first cap can be secured to a graft body before the graft body is delivered to a fistula tract, while a second cap can be secured to the graft body after delivery.

Passages formed or otherwise occurring in a graft body (such as the passages 207 shown in FIG. 12) may be present in any suitable number and form. These passages can exhibit a variety of shapes and sizes, and can extend through all or a portion of the body. In some forms, one or more passages extend from a graft body surface and include a generally coherent passage wall. Illustratively, a tubular graft body having an internal lumen extending through the body along its length can have passages extending partially or entirely through a wall of the tube, e.g., from an exterior surface to an interior surface of the tube wall. Also, the spacing and size of a passage in a graft body relative to another passage in the body, as well as the depth to which a particular passage extends into a graft body, can vary. In some forms, the passages are generally cylindrical voids, e.g., having diameters ranging from about 0.05 mm to about 15 mm, more typically from about 0.10 mm to about 5 mm, and even more typically from about 0.1 mm to about 1.0 mm. These and other graft body passages useful in the present invention can be spaced any suitable distance from one another, and in some embodiments, are positioned in a particular pattern (e.g., in rows), although a plurality of passages can be randomly placed as well. Further, a plurality of passages in a construct can be configured so that any one passage extends the same or a different distance into the construct relative to any other passage in the construct.

In other embodiments of the present invention, the graft comprises an elongate graft body and an expandable cap. Such grafts can include multiple expandable caps, and in some cases, include at least one expandable cap and at least one non-expandable cap. An expandable cap useful in the invention may comprise an expandable device including but not limited to a resilient wire frame formed with a metallic or synthetic polymeric material. In some aspects, an expandable cap comprises a material having the capacity to expand (e.g., a naturally occurring material such as a collagen-containing material or a non-naturally occurring material such as a synthetic polymeric-containing material). Illustratively, an expandable cap comprises a sponge-form material containing an ECM material such as pericardium, submucosa or basement membrane.

Figure 13:
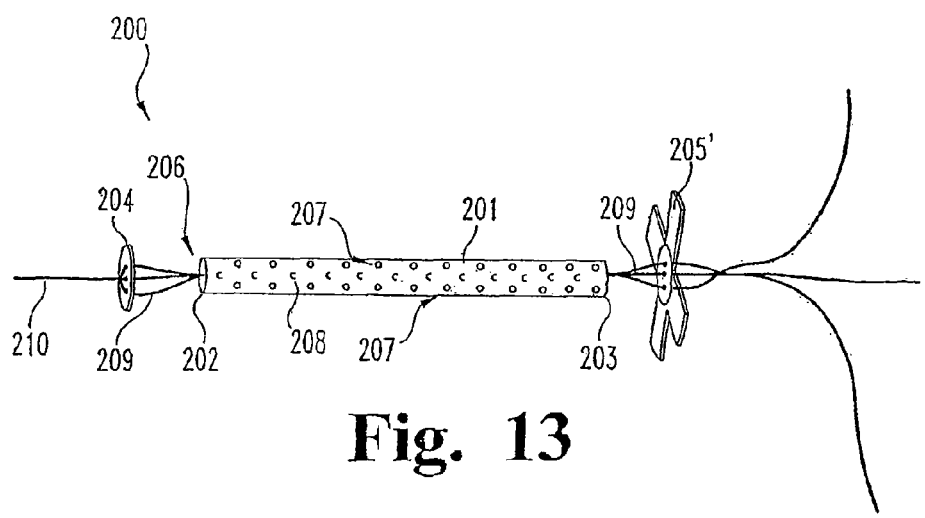
FIG. 13 shows another embodiment of the graft of the present invention, similar to the embodiment of FIG. 12 but with an expandable cap.

With reference now to FIG. 13, shown is another embodiment of the fistula plug of the present invention. This plug is similar to that shown in FIG. 12 except that second cap 205' is expandable. In one mode of using such a plug, an appropriately-sized, dried plug body 201 is selected to suit the particular fistula being treated. The first cap 204 and expandable second cap 205' (which are loosely retained in association with plug body 201 by suture strand 209) may then be attached to first graft body end 202 and second graft body end 203, respectively, using suitable attachment means (e.g., an adhesive, sutures and/or the like). Next, the dried plug body 201 may be at least partially hydrated (optional) and then, in the case of a recto-vaginal fistula, for example, deployed by passing the second graft body end 203 through the fistula opening on the rectal side and advancing it toward the fistula opening on the vaginal side. This step may be facilitated by receiving the fistula plug over an emplaced guidewire. The plug body 201 is then advanced until the first cap 204 contacts portions of the rectal cavity wall adjacent to the fistula opening. Plug body 201 can be advanced through the fistula tract in any suitable manner, and in some forms, is pulled through the tract by pulling on suture strand 209. Advantageously, plug body 201 will be sized and adapted so that upon being pulled into position (i.e., with the first cap 204 contacting the rectal cavity wall), the expandable second cap 205' will be located at the fistula opening on the vaginal side and in a position to contact patient tissue adjacent to (or otherwise in and/or around) this vaginal-side opening upon expanding. The expandable second cap 205' can move between a first, compacted position and a second, expanded position. When compacted, the second cap 205' can be passed through the fistula tract. Once expanded, the second cap 205' contacts patient tissue around the vaginal side opening and thus resists withdrawal back through the fistula tract. If present, the guidewire 210 can then be removed, and suture strand 209 can be trimmed as necessary.

In some embodiments of the present invention, the fistula graft includes a cap, an elongate graft body extending from the cap, and an additional cap that can be positioned at different locations along the graft body to provide adjustability to the overall graft. In use, this additional cap may be effective, in certain aspects, to contact patient tissues in and around a fistula opening to block and/or fill the opening, and in some cases, to seal the opening. Such a cap may be translatable along the graft body, and in some embodiments, may be received over and slid along the graft body so that the distance between the first cap and the second cap can be adjusted. Other adjustable devices useful in the present invention include, but are not limited to, a cap that can be positioned along the graft body, yet does not slide over the graft body. Illustratively, such a cap or other suitable device can be clamped onto or otherwise attached to the graft body from the side.

With reference now to FIG. 14, shown is a perspective view of a fistula graft 300 of the present invention which can be used to treat fistulas such as recto-vaginal fistulas, for example. Fistula graft 300 includes a biocompatible graft body 303 that is configured to block at least a segment of a fistula, e.g., a fistula tract and/or one or more fistula openings such as a primary opening or secondary opening. The graft 300 includes a first cap 302, a graft body 303 that extends from the cap 302, and a distal end 304. The first cap 302, which may be formed from a synthetic material (such as Nylon), may generally take any suitable form (such as the form of a disk) and configured to contact portions of tissue adjacent to a fistula opening. One side of the cap 302 may include a generally disk-shaped cavity (having a diameter smaller than that of the first cap 302) in which a disk-shaped gasket 305 resides, as shown in FIGS. 14 and 16. Gasket 305 may be formed from a tissue ingrowth material, and may be attached to the cap 302 with absorbable sutures 306, although the two may be attached or otherwise held together in any suitable manner. The graft body 303, which may be formed from an ECM material, may generally take the shape of a cylinder and be configured to extend into at least a portion of a fistula tract.

The graft 300 may also include a second cap 307 which may be received over the distal end 304 and configured to slide along the graft body 303. In some embodiments, the second cap is formed with a vacuum pressed ECM material such as SIS. To create such an opening through which the graft body 303 can be received, portions of the second cap 307 may be cut (and in some cases removed). In the embodiment shown in FIGS. 14 and 15, an X-shaped cut in the second cap 307 provides flaps 308. In other embodiments, cuts of other shapes may be made to provide an opening through which a fistula plug can be received, including but not limited to, a circular cut or an S-shaped cut. Flaps 308 may be useful in securing second cap 307 to graft body 303, e.g., by adhering or suturing the flap(s) 308 to the graft body 303.

In one mode of operation, graft body 303 is deployed by passing the distal end 304 of the graft body 303 (with the second cap 307 removed from the graft body) through a first fistula opening (e.g., an opening in a rectal cavity wall) and advancing it through the fistula tract and toward a second fistula opening (e.g., an opening in a vaginal cavity wall). This step may be facilitated by receiving the graft over an emplaced guidewire (in which case graft body 303 would need to be adapted to be able to receive such a device). The graft body 303 may then be advanced until the first cap 302 and gasket 305 contact portions of the tissues adjacent to the first fistula opening. By maintaining this contact for a sufficient period of time, new tissue can grow into the gasket 305, which can promote and/or facilitate blockage of the fistula opening, and in some cases, sealing off of the opening. The graft body 303 can be advanced through the fistula tract in any suitable manner, and in some embodiments, is pulled through the tract by pulling on a suture strand which is connected to or otherwise associated with (e.g., threaded through) the graft body 303. In other embodiments, a grasping device such as surgical hemostasis is used to pull the graft into position. In general, the graft body 303 will be sized so that upon being pulled or pushed into position (i.e., with the first cap 302 and gasket 305 contacting portions of the tissues adjacent to the first fistula opening), the distal end 304 of the graft body 303 will extend beyond the second fistula opening. The second cap 307 can then be received over the graft body distal end 304 and advanced until it contacts portions of the tissue wall adjacent the second fistula opening. The second cap 307 is then attached to the graft body 303, e.g., by suturing flaps 308 to the graft body, and any excess portion of distal end 304 can be removed (e.g., trimmed) as desired. If a guidewire is present, it can then be removed. In some embodiments, the graft 300 is similarly deployed except that the distal end 304 of the graft body 303 is first passed through a fistula opening occurring in a vaginal cavity wall so that it extends beyond an opening occurring in a rectal cavity wall.

The first cap 302 and gasket 305 may or may not include one or more of the same materials. In one embodiment, the gasket 305 is formed with a tissue ingrowth material, and the first cap 302 is formed with a material having relatively less receptivity to tissue ingrowth, and in some embodiments, with a material having very little or no receptivity to tissue ingrowth. Illustratively, the first cap 302 can be formed with a rigid or semi-rigid synthetic polymeric material, and the gasket 305 can be formed with a pliable remodelable collagenous material.

Seal enhancement devices such as gasket 305 come in a variety of shapes and sizes, and can be configured in variety of manners in and around a cap to promote and/or facilitate sealing off of a fistula opening. In addition to gasket 305, the present invention provides other devices and materials which can be incorporated into or otherwise associated with a cap to provide an enhanced seal between the cap and the tissues adjacent to the fistula opening. In some embodiments, such devices comprise a flowable or sheet-form tissue ingrowth material residing in and/or on a cap.

Figure 17:
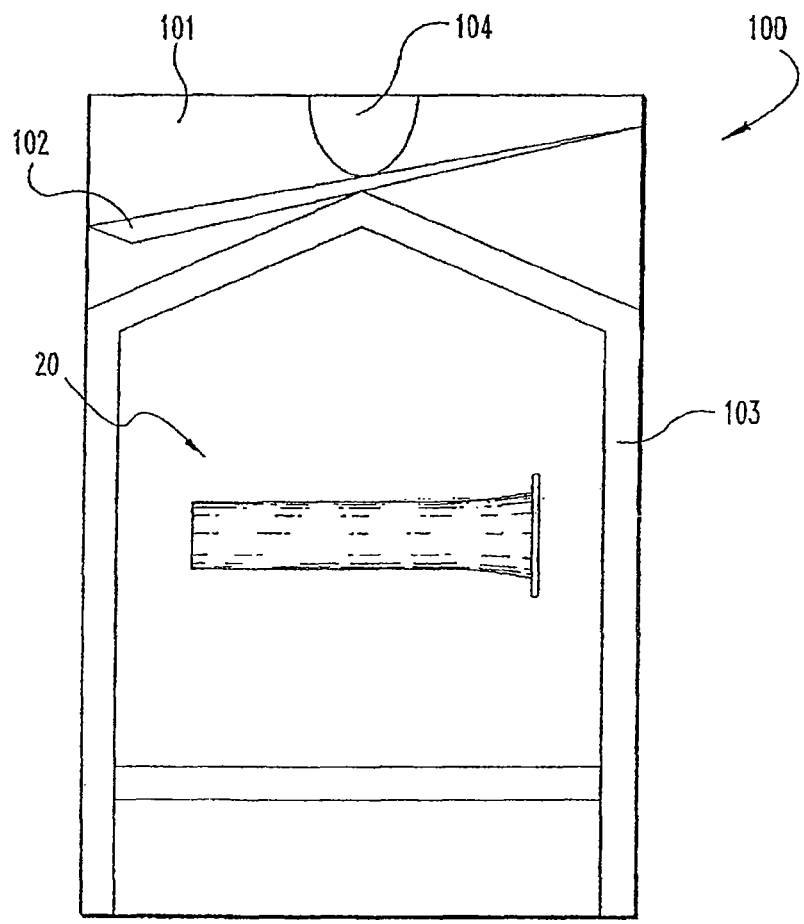
FIG. 17 is a top view of one embodiment of a medical product of the present invention.

With reference now to FIG. 17, shown is a top view of an illustrative medical product 100 of the present invention that includes a graft 20 sealed within sterile medical packaging. In particular, medical product 100 has packaging including a backing layer 101 and a front film layer 102 (shown partially drawn away from the backing layer 101). The graft 20 is sealed between the backing layer 101 and the film 102 by a boundary of pressure-adhesive 103, which may be of any suitable shape and size. A cut-out 104 may be provided in the backing layer 101 to assist a user in separating the film layer 102 from the backing layer 101.

Sterilization of the medical product 100 may be achieved, for example, by irradiation, ethylene oxide gas, or any other suitable sterilization technique, and the materials and other properties of the medical packaging can be selected accordingly. Also, grafts of the invention can be contained in sterile packaging in any suitable state. Suitable states include, for example, a hydrated or dehydrated state. The grafts can be dehydrated by any means known in the art (e.g., lyophilization or air dried). If a graft of the present invention is stored in a dehydrated state, it is preferred that it retains all of its biological and mechanical properties (e.g., shape, density, flexibility, etc.) upon rehydration.

The materials and other properties of the packaging can be selected according to the needs and desires of the end user of the product contained therein. For example, the package can include indicia to communicate the contents of the package to a person and/or a machine, computer, or other electronic device. Such indicia may include the dimensions of, the type of materials used to form, and/or the physical state of, the contents of the package. In certain embodiments, a graft is packaged for sale with instructions for use. For example, in particularly preferred embodiments, a medical product includes at least one graft (including a graft body, one or more caps, and/or a tail, as distinct components or as an integral unit) sealed within a sterile package, wherein the packaging has visible indicia identifying the graft and/or the graft components as having certain physical characteristics. The packaging may contain or otherwise be associated with printed materials identifying the contents as having such physical characteristics and including information concerning its use as a graft for treating fistulas. The packaging may also include visible indicia relating to the dimensions of the graft, and/or relating to the treatment site(s) for which the graft is configured.

The present invention also provides a line of medical products that include one or more grafts or graft components, such as those described herein, enclosed within a sealed package. When the medical product includes a plurality of grafts or graft components, the products can each be of substantially the same size and shape, or, alternatively, can vary with respect to size and shape.

Turning now to a discussion of the materials that may be used to form the graft of the present invention, the graft may be made of any biocompatible material suitable for implantation into a mammalian body. Desirably, the graft is made of a single, non-allergenic biological or synthetic material. More desirably, the graft is made of a remodelable material.

Suitable biological materials may be rendered non-cellular during processing to avoid immunological rejection. Such biological tissues may be implanted in potentially infected surgical fields and resist infection, unlike some synthetic preparations that may elicit a foreign body reaction or act as a nidus for infection. Suitable biological materials that may be used in the present invention include, but are not limited to, heterograft material (i.e., cross-species material, such as tissue material from a non-human donor to a human recipient), allograft material (i.e., tissue material from a human cadaveric donor), and/or autograft material (i.e., where the donor and the recipient are the same individual). Desirably, the material promotes angiogenesis and/or site-specific tissue remodeling. Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

Autograft tissue is grown from a skin biopsy of the patient. Once the fibroblasts have regenerated and formed enough new tissue, the new tissue may be injected back into the surgical site of the same patient. This process takes several weeks to complete, but avoids tissue rejection and disease transmission. One such product is Isolagen (Isolagen Inc.—Houston, Tex.).

Suitable cadaveric materials include, but are not limited to, cadaveric fascia and cadaveric dura matar. Specific suitable cadaveric allografts include, but are not limited to, AlloDerm, (LifeCell Corp.—Branchburg, N.J.), Cymetra, (LifeCell Corp.—Branchburg, N.J.), Dermaloga, Fascion (Fascia Biosystems, LLC—Beverly Hills, Calif.), and Suspend (Mentor—Irving, Tex.). These products are freeze-dried, or lyophilized, acellular dermal tissue from cadaveric donors. Some require reconstitution before implantation. Although disease transmission or antigenic reaction is possible, the risk may be minimized by an extensive screening and processing of the material.

Heterograft materials are taken from a donor of one species and grafted into a recipient of another species. Examples of such materials include, but are not limited to, Surgisis (Cook Surgical—Bloomington, Ind.), Permacol (TSL—Covington, Ga.), Pelvicol (Bard Inc.—Murray Hill, N.J.) and Peri-Guard, (Bio-Vascular Inc.—St Paul, Minn.). In one embodiment of the present invention, an injectable heterograft, such as a heterograft of small intestinal submucosa or other material having a viscosity sufficient to prevent the material from running out or being squeezed out of the fistula, is used.

The materials used to form the grafts of the present invention should generally be biocompatible, and in desirable embodiments, are comprised of a remodelable material. Desirably, the material has a collagenous tissue frame that remains intact to allow for ingrowth of host cells and eventual reconstruction of the host tissue itself. Desirable remodelable collagenous materials can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a graft of the invention is implanted, e.g., around tissue defining a fistula tract or an opening to a fistula.

Suitable remodelable materials can be provided by collagenous extracellular matrix (ECM) materials possessing biotropic properties. For example, suitable collagenous materials include ECM materials such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer that may be used in the invention ranges from about 50 to about 250 microns when fully hydrated, and more typically from about 50 to about 200 microns when fully hydrated, although isolated layers having other thicknesses may also be obtained and used. These layer thicknesses may vary with the type and age of the animal used as the tissue source. These layer thicknesses may also vary with the source of the tissue obtained from the animal source.

In some embodiments of the present invention, one or more bioactive agents are included. As used herein, the phrase "bioactive agent" refers to any pharmaceutically active agent that produces an intended therapeutic effect on the body to treat or prevent conditions or diseases. Such bioactive agents may be incorporated into the graft material(s), coated onto the graft material(s), or included in the graft (or portions thereof) in any other suitable manner. For example, a bioactive agent (or a bioactive agent combined with another biocompatible material) may be coated on a graft body or contained in passages formed in a graft body, and be configured to release over a certain period of time.

Suitable bioactive agents may include one or more bioactive agents native to the source of the ECM tissue material. For example, a submucosa or other remodelable ECM tissue material may retain one or more growth factors including but not limited to basic fibroblast growth factor (FGF-2), transforming growth factor beta (TGF-beta), epidermal growth factor (EGF), cartilage derived growth factor (CDGF), and/or platelet derived growth factor (PDGF). In addition, submucosa or other ECM materials when used in the invention may retain other native bioactive agents including but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

In addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to material layers include, for example, anti-clotting agents, e.g. heparin, antibiotics, anti-inflammatory agents, and anti-proliferative agents, e.g. taxol derivatives such as paclitaxel. Such non-native bioactive components can be incorporated into and/or onto ECM material in any suitable manner, such as by surface treatment (e.g., spraying) and/or impregnation (e.g., soaking), just to name a few non-limiting examples.

Other suitable bioactive agents that may be used in the present invention include, but are not limited to: antithrombotics, including but are not limited to anticoagulants (such as thrombin, Factor Xa, Factor VIIa, tissue factor inhibitors, heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717), antiplatelets (such as glycoprotein IIb/IIIa, thromboxane A2, ADP-induced glycoprotein IIb/IIIa, phosphodiesterase inhibitors, eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds), and fibrinolytics (such as plasminogen activators, thrombin activatable fibrinolysis inhibitor (TAFI) inhibitors, other enzymes which cleave fibrin, alfimeprase, alteplase, anistreplase, reteplase, lanoteplase, monteplase, tenecteplase, urokinase, streptokinase, or phospholipid encapsulated microbubbles; and other bioactive materials such as endothelial progenitor cells or endothelial cells).

Still other non-limiting examples of suitable bioactive agents that may be used in the present invention include, but are not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) II/III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

ECM materials used in the present invention may be free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from about 2 to about 10 epoxide groups per molecule.

In certain embodiments, the present invention provides grafts including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. In addition, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously pressing the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher (e.g., no higher than about 38° C.) will preferably be used in some forms of the present invention. These include, for example, vacuum pressing operations at less than about 38° C., forced air drying at less than about 38° C., or either of these processes with no active heating—at about room temperature (i.e., about 25° C.) or with cooling. Relatively low temperature conditions also, of course, include lyophilization conditions.

Grafts of the present invention may include biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Suitable biocompatible grafts of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polygalactin, hyaluronic acid, polydioxanone, polyorthoester, polyanhydride, poly(glycolic acid), poly(D,L-lactic acid), poly(glycolic acid-co-trimethylene carbonate), polyhydroxylkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Desirably, the biological or synthetic material used in the present invention assists in reconstruction of the host tissues, elicits little immunological reaction, and has some inherent resistance to infection. Such material may desirably allows incorporation of the graft into the host tissue of the fistula (rather than complete absorption of the graft into the surrounding tissue), thereby occluding the fistula.

In one embodiment of the present invention, a drug, such as an antibiotic, is incorporated into the graft, as an extra precaution or means of treating any residual infection within the fistula. The graft may also be used in conjunction with a sealant or sclerosing solution which may be injected into the main fistula tract and any side branches. Several possible sealants are described in the prior art. One of the more commonly used sealants is fibrin glue, known as Tisseal (Baxter Inc.). The glue is prepared by mixing coagulation activation factors with fibrinogen, which react to form fibrin. The fibrin forms a matrix, which acts as a scaffold for tissue ingrowth and results in the sealing of the fistula tract.

Turning now to a general discussion regarding methods for treating fistulas according to the present invention, suitable treatment methods include providing a graft, such as any of those described herein, and implanting the graft within a patient so that: (i) the graft blocks at least the primary opening of a fistula, i.e., the primary opening and potentially one or more other segments of a fistula, for example, the fistula tract and/or any secondary openings; (ii) the cap contacts portions of the tissues adjacent to the primary opening and/or portions of the tissues surrounding any secondary openings; and (iii) the graft body extends into at least a portion of the fistula tract. The grafts and methods of the present invention can be used to treat any fistula, such as a fistula having a primary opening in a wall of an alimentary canal. In some aspects, the invention provides grafts and methods useful for blocking openings anywhere on or within the body of a patient, for example, blocking at least the primary opening of a urethro-vaginal fistulas, vesico-vaginal fistulas, tracheo-esophageal fistulas, gastro-cutaneous fistulas, fistulas occurring between the vascular and gastrointestinal systems, and any number of anorectal fistulas, such as recto-vaginal fistula, recto-vesical fistulas, recto-urethral fistulas, or recto-prostatic fistulas. Also, inventive products and methods can be used to treat a fistula regardless of its size and shape, and in some forms, are used to treat fistulas having a primary opening, secondary opening(s), and/or fistula tract with a diameter ranging from about 1 to about 20 millimeters, more typically from about 5 to about 10 millimeters.

Grafts of the invention can be implanted using any suitable delivery method or placement technique. Illustratively, a graft body can be implanted by pulling or pushing the graft body into a suitable position within a fistula. In some embodiments of the present invention, the graft includes a tail in association with the graft body, for example, sutured, glued, tied, or attached by another suitable means to the graft body. This tail can be used to pull the graft body into a suitable position within a fistula. For example, the distal end of the graft body or the tail of the graft can be pulled through the primary opening of the fistula and towards the secondary opening until the cap contacts portions of the alimentary canal wall adjacent to the primary opening and/or the proximal end of the graft body becomes wedged into the primary opening, as described above. In certain embodiments, such implantation can be accomplished using a fistula probe or scope or another suitable instrument, for example, an appropriately configured pair of surgical hemostats that includes a portion passable into a secondary opening, through the fistula tract, and potentially out of the primary opening. Thereafter, the graft body can be releasably grasped by the probe or otherwise coupled to the probe and pulled into the primary opening. The graft body may also be secured at one or both ends by means of sutures, cap(s), or any other suitable method of affixation.

In some embodiments of the present invention, the tail of the graft is used to sufficiently locate a suitable fistula graft within a patient, and then is removed from the graft, for example, using cutting shears. In alternative embodiments, the tail is made from a remodelable or otherwise absorbable material such that it can be left in place within the fistula tract. In these forms, the absorbable tail can be used to anchor or otherwise suitably secure the fistula graft within the implantation site. For example, the tail can be tied to the tissues of the patient at a suitable location, for example, a location just inside or external to a secondary fistula opening. Further, in alternative embodiments, an illustrative fistula graft can be positioned so that it spans the entire length of a fistula tract, i.e., from the primary opening to a location at or external to a secondary opening. In these embodiments, string or suture, for example, can be used to secure the tail of the graft to the tissue of the patient at an external location.

In some embodiments of the method of the present invention, after implanting a graft into a fistula tract, either end of the graft or both ends of the graft are secured by sutures to ensure that the graft is not displaced and/or expelled through the primary opening or the secondary opening. The suture may be formed as an integral part of the graft or as a separate component. Where the graft includes a cap on the proximal end of the graft body, it may be desirable to secure the distal end of the graft at the level of the secondary opening for additional assurance that the graft will not be displaced or expelled through the primary opening. The means of securing the distal end of the graft may be similar to those used to secure the proximal end of the graft or may be any other suitable means of securement. The use of a cap on each end of the graft may be desirable to avoid the need for using sutures and piercing the tissues of the patient to firmly secure the graft within the fistula tract.

Fistula treatment methods of the invention may include an endoscopic visualization (fistuloscopy) step, as disclosed in co-pending application Ser. No. 10/945,634 (Armstrong), hereby incorporated by reference in its entirety. Such endoscopic visualization can be used, for example, to determine the shape and size of the fistula, which in turn can be used to select an appropriately sized and shaped graft for treating the fistula. Illustratively, a very thin flexible endoscope can be inserted into a secondary opening of the fistula and advanced under direct vision through the fistula tract and out through the primary opening. By performing fistuloscopy of the fistula, the primary opening can be accurately identified. Also, cleaning of the fistula can be performed prior to and/or during deployment of a graft of the invention. For example, an irrigating fluid can be used to remove any inflammatory or necrotic tissue located within the fistula prior to engrafting the product. In certain embodiments, one or more antibiotics are applied to the graft and/or the soft tissues surrounding the fistula as an extra precaution or means of treating any residual infection within the fistula.

In some embodiments of the method of the present invention, a fistula is drained prior to receiving a graft of the invention therein. Such draining can be accomplished by inserting a narrow diameter rubber drain known as a seton through the fistula. The seton is passed through the fistula tract and tied as a loop around the contained tissue and left for several weeks or months. This procedure is usually performed to drain infection from the area, and to mature the fistula tract prior to a definitive closure procedure.

The grafts of the present invention can be modified before, during, and/or after deployment. Illustratively, the graft may be cut, trimmed, sterilized, and/or treated (e.g., brought into contact, impregnated, coated, etc.) with one or more desirable compositions, such as any of those disclosed herein, e.g., anticoagulants (e.g., heparin), growth factors or other desirable property modifiers. In certain aspects, following deployment of a graft in accordance with the present invention, one or more portions of the graft, for example, material protruding from the primary opening and/or any secondary opening, are trimmed off or otherwise removed.

In other embodiments, the graft is anchored within the fistula by threading a securing device having a central lumen, over the tail of the graft and securing it into position at skin level (e.g., by crimping it). In yet another embodiment, further anchoring of the graft is achieved by using a material such as a small intestinal submucosa heterograft (a freeze-dried material that requires rehydration before use) for the graft and inserting the graft into the tract before the graft material has been fully expanded by hydration. Any other suitable means of securement, such as introducing adhesive into the fistula tract, may also be used to anchor the graft within the fistula.

In one embodiment, autologous fibrin glue is used in conjunction with the fistula graft to supplement the adhesive and occlusive properties of the disclosed invention (e.g., *Symphony PCS*, DePuy AcroMed Inc.). This involves the use of an autologous composite of platelets and growth factors derived from the patient's own blood. The composite may be derived from a fresh sample of blood drawn from the patient at the time of surgery. The blood may then be centrifuged, and the platelets, which contain growth factors such as epidermal growth factor (EGF) and transforming growth factor-beta (TGFβ), harvested. Having centrifuged the blood, retrieved the platelet "pellet" and prepared the composite, the sealant may then be injected into the fistula tract(s) to help maintain the graft in place.

Closure of a fistula tract may be performed as a one-stage or two-stage procedure. As a one-stage procedure, the fistula tract is closed or sealed at the same time as the initial surgery. The primary advantage of this method is that it avoids a second operation and minimizes expense and inconvenience. However, immediate implantation of the graft into an unprepared and possibly infected fistula tract may result in a secondary infection. As a two-stage procedure, a seton is first placed through the fistula tract to allow mechanical drainage of the fistula tract. Several weeks later, the seton is removed and the graft is inserted into the fistula. In certain embodiments of the method of the present invention, a tail associated with the graft body is used to eliminate the seton placement step.

Turning now to particular methods of the invention for delivering fistula plugs such as that shown in FIG. 12 to a fistula tract, such as a recto-vaginal fistula, in one mode of operation, preparing an inventive plug for use includes selecting an appropriately-sized, dried plug body 201 for the particular fistula being treated. This may involve a pre-implantation measurement step where one or more dimensions of a fistula such as the fistula tract length, diameter, etc., are determined. In some cases, a graft body may need to be altered before or during implantation, for example, trimmed lengthwise to suit a particular fistula tract length. The loosely retained first cap 204 may then be attached to first plug body end 202 using additional suture material or another suitable attachment means (e.g., stapling or bonding with an adhesive). Next, the dried plug body 201 may be at least partially hydrated (optional), and then deployed by passing the second plug body end 203 through a fistula opening on the rectal side and advancing it toward the fistula opening on the vaginal side. This step may be facilitated by receiving the fistula plug over an emplaced guidewire 210. The plug body 201 may then be advanced until the first cap 204 contacts portions of the rectal cavity wall adjacent to the fistula opening. Bonding agents, sutures, mechanical fasteners and/or other suitable securing means may be used in certain embodiments to maintain or at least help maintain this contact. Plug body 201 can be advanced through the fistula tract in any suitable manner, and in some forms, is pulled through the tract, e.g., by pulling on suture strand 209. Suture strand 209 may then be passed through apertures in the second cap 205, and the second cap 205 may be threaded onto the guidewire (if present). In advantageous embodiments, the plug body 201 will be sized so that, upon being pulled into position (i.e., with the first cap 204 contacting the rectal cavity wall), the second plug body end 203 will be generally flush with the tissue surrounding the fistula opening on the vaginal side. Alternatively, the second plug body end 203, when pulled into position, will extend beyond the fistula opening on the vaginal side, and in this case, can be trimmed as desired (e.g., to be generally flush with the vaginal cavity wall). The second cap 205 is then attached to the second plug body end 203. If present, the guidewire can then be removed, and suture strand 209 can be trimmed as necessary.

In alternative embodiments, suture material can be passed through central lumen 206 and directly bonded to one or more caps. This suture material can provide means for adjusting graft body positioning during and/or after deployment, and potentially also provide means for anchoring the plug body 201 during a deployment step, for example, by suturing plug body 201 to patient tissue at or adjacent to a fistula opening.

Passages occurring in a graft body, such as those depicted in FIG. 12, may be formed in any suitable manner. In some embodiments, passages can be created in a graft body after the graft body is formed, e.g., after a cast collagenous material is dried to form a coherent body. In some embodiments, at least part of the formation of some or all of the passages in a graft body occurs during formation of the graft body. Illustratively, an inventive method can include a step where a passage is initially provided in a hydrated material mass, e.g., by displacing a volume of material in the mass. Then, with the passages present in the hydrated material mass, the mass can be subjected to suitable drying conditions (e.g., a lyophilization step) to cause or allow the passages to be retained in the dried graft body. It should be noted that a hydrated material in such processes (e.g., a reconstituted or naturally-derived collagenous material) can have a level of hydration including full or partial hydration, and in this regard, a drying process can be used to lower starting material hydration to any suitable level including substantially dehydrated. Also, displacing a volume of material in a hydrated mass of material to create a passage can be accomplished in a variety of manners, and in certain aspects, involves forcing or otherwise introducing an implement or other material-displacing object (e.g., a cannulated or non-cannulated needle) into the mass. Other suitable material-displacing objects can be selected according to the type of passage desired.

These and other inventive graft body formation methods can involve manipulating graft material within a mold or form. It should be noted that the graft material may or may not be hydrated when placed in, on, around, etc. a mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct. In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In some embodiments, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Although not necessary to broader aspects of the invention, in some embodiments, the formation of such a graft construct comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide a graft body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid graft body as discussed herein.

In some aspects of the invention, where multiple fistulas are present, multiple grafts may be inserted until all fistula tracts have been closed. In the case of a complex fistula, for instance a horseshoe fistula, there may be one primary opening and two or more tracts leading from that opening. In this instance, a graft may be configured with one proximal end (e.g., a larger diameter end), and two distal ends (e.g., smaller diameter ends). Desirably, accurate identification of all fistula tracts and the primary opening is facilitated by first performing fistuloscopy. Once the entire tract has been identified and cleaned out, each tail may be pulled through the primary opening into each fistula in turn, desirably using a fistulascope or an instrument passed through the instrument channel of a scope. Adequate force may be applied to the tail to ensure that the proximal end of the graft body is firmly secured in the primary opening and/or the cap attached to the proximal end of the graft body contacts the alimentary canal wall adjacent to the primary opening. The proximal end of the graft and/or each of the tails may be further secured by any of the methods described above.

The closure of fistulas with the grafts and methods of the present invention results in minimal cutting or piercing of tissue (if any), sphincter damage, and incontinence. In addition, the current invention simplifies the implantation procedure and prevents dislodgement of the grafts.

All publications and patent applications cited in this specification are hereby incorporated by reference in their entirety, as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

We claim:

1. A fistula graft for treating a fistula having an opening in a first tissue wall, an opening in a second tissue wall, and a fistula tract extending therebetween, the fistula graft comprising:
    a first cap;
    an elongate graft body having a first end attached to the first cap and a second end, the graft body comprising remodelable material selected from the group consisting of a cadaveric material from a human donor and a heterograft material from a non-human donor, and
    a gasket having a lumen, wherein the elongate graft body extends through the lumen and wherein the gasket is positioned against the first cap.

2. The fistula graft of claim 1, wherein the elongate graft body comprises a rolled or folded intact, acellular sheet of remodelable material that promotes cellular invasion and ingrowth within the acellular sheet and reconstruction of host tissue within the acellular sheet.

3. The fistula graft of claim 1, wherein the graft body comprises a remodelable material selected from the group consisting of submucosa, renal capsule membrane, dermal collagen, dura mater, pericardium, serosa, peritoneum, basement membrane layers, and liver basement membrane.

4. The fistula graft of claim 3, wherein the remodelable material is selected from the group consisting of submucosa and dermal collagen.

5. The fistula graft of claim 1, wherein the first cap is integral with the elongate graft body and formed from the same material as the elongate graft body.

6. The fistula graft of claim 1, wherein the first cap is affixed to the elongate graft body in a non-permanent manner.

7. The fistula graft of claim 6, wherein the first cap is affixed to the elongate graft body by a suture.

8. The fistula graft of claim 1, wherein the first end of the elongate graft body is larger than the second end and wherein the elongate graft body comprises a taper between the first end and the second end.

9. The fistula graft of claim 1, wherein the first cap comprises an absorbable material.

10. The fistula graft of claim 1, wherein the gasket comprises an intact, acellular sheet of remodelable material that promotes cellular invasion and ingrowth within the acellular sheet and reconstruction of host tissue within the acellular sheet.

11. The fistula graft of claim 1, wherein the remodelable material is submucosa.

12. The fistula graft of claim 1, wherein the gasket attaches to the first cap by a suture.

13. The fistula graft of claim 1, wherein the elongate graft body is cylindrical.

14. A fistula graft for treating a fistula having an opening in a first tissue wall, an opening in a second tissue wall, and a fistula tract extending therebetween, the fistula graft comprising:
   a first cap; and
   an elongate graft body having a first end attached to the first cap and a second end, the graft body comprising remodelable material selected from the group consisting of a cadaveric material from a human donor and a heterograft material from a non-human donor, wherein the first cap attaches to the first end of the elongate graft body in a manner resulting in detachment and release of the first cap from the elongate graft body following implantation of the fistula graft in the fistula.

15. The fistula graft of claim 14, wherein the remodelable material is selected from the group consisting of submucosa and dermal collagen.

16. The fistula graft of claim 14, wherein the first cap comprises an absorbable material.

17. The fistula graft of claim 14, wherein the first cap comprises a synthetic polymeric material.

18. The fistula graft of claim 14, wherein the remodelable material is selected from the group consisting of submucosa, renal capsule membrane, dermal collagen, dura mater, pericardium, serosa, peritoneum, basement membrane layers, and liver basement membrane.

19. The fistula graft of claim 14, wherein a bioabsorbable suture attaches the first end of the elongate graft body to the first cap and wherein the attachment is such that the cap detaches from the elongate graft body upon absorption of the suture.

* * * * *

UNITED STATES PATENT AND TRADEMARK OFFICE
CERTIFICATE OF CORRECTION

PATENT NO. : 8,501,217 B2
APPLICATION NO. : 13/018582
DATED : August 6, 2013
INVENTOR(S) : David N. Armstrong et al.

It is certified that error appears in the above-identified patent and that said Letters Patent is hereby corrected as shown below:

On the Title Page

Item (75), Inventors, replace "Brain L. Bates," with --Brian L. Bates,--.

Signed and Sealed this
Eighth Day of October, 2013

Teresa Stanek Rea
*Deputy Director of the United States Patent and Trademark Office*